US007588897B2

(12) United States Patent
Pollner et al.

(10) Patent No.: US 7,588,897 B2
(45) Date of Patent: Sep. 15, 2009

(54) COMPOSITIONS AND METHODS TO DETECT *ENTEROCOCCI* NUCLEIC ACID

(75) Inventors: Reinhold B. Pollner, San Diego, CA (US); Kristin W. Livezey, Encinitas, CA (US)

(73) Assignee: Gen-Probe Incorporated, San Diego, CA (US)

( * ) Notice: Subject to any disclaimer, the term of this patent is extended or adjusted under 35 U.S.C. 154(b) by 68 days.

(21) Appl. No.: 11/747,314

(22) Filed: May 11, 2007

(65) Prior Publication Data

US 2007/0264658 A1 Nov. 15, 2007

Related U.S. Application Data

(60) Provisional application No. 60/800,116, filed on May 12, 2006.

(51) Int. Cl.
C12Q 1/68 (2006.01)
C12P 19/34 (2006.01)
C07H 21/04 (2006.01)

(52) U.S. Cl. .................. 435/6; 435/91.2; 536/24.32; 536/24.33

(58) Field of Classification Search ................... None
See application file for complete search history.

(56) References Cited

U.S. PATENT DOCUMENTS

| | | | |
|---|---|---|---|
| 4,581,333 A | 4/1986 | Kourilsky et al. |
| 4,683,195 A | 7/1987 | Mullis et al. |
| 4,683,202 A | 7/1987 | Mullis |
| 4,786,600 A | 11/1988 | Kramer et al. |
| 4,800,159 A | 1/1989 | Mullis et al. |
| 4,868,105 A | 9/1989 | Urdea et al. |
| 5,118,801 A | 6/1992 | Lizardi et al. |
| 5,124,246 A | 6/1992 | Urdea et al. |
| 5,130,238 A | 7/1992 | Malek et al. |
| 5,283,174 A | 2/1994 | Arnold, Jr. et al. |
| 5,312,728 A | 5/1994 | Lizardi et al. |
| 5,378,825 A | 1/1995 | Cook et al. |
| 5,399,491 A | 3/1995 | Kacian et al. |
| 5,422,252 A | 6/1995 | Walker et al. |
| 5,424,413 A | 6/1995 | Hogan et al. |
| 5,427,930 A | 6/1995 | Birkenmeyer et al. |
| 5,437,990 A | 8/1995 | Burg et al. |
| 5,451,503 A | 9/1995 | Hogan et al. |
| 5,516,663 A | 5/1996 | Backman et al. |
| 5,521,300 A | 5/1996 | Shah et al. |
| 5,547,842 A | 8/1996 | Hogan et al. |
| 5,547,861 A | 8/1996 | Nadeau et al. |
| 5,554,516 A | 9/1996 | Kacian et al. |
| 5,585,481 A | 12/1996 | Arnold, Jr. et al. |
| 5,639,604 A | 6/1997 | Arnold, Jr. et al. |
| 5,648,211 A | 7/1997 | Fraiser et al. |
| 5,656,207 A | 8/1997 | Woodhead et al. |
| 5,658,737 A | 8/1997 | Nelson et al. |
| 5,824,518 A | 10/1998 | Kacian et al. |
| 5,849,481 A | 12/1998 | Urdea et al. |
| 5,925,517 A | 7/1999 | Tyagi et al. |
| 5,958,695 A | 9/1999 | Mankin |
| 6,110,678 A | 8/2000 | Weisburg et al. |
| 6,150,097 A | 11/2000 | Tyagi et al. |
| 6,180,340 B1 | 1/2001 | Nelson |
| 6,280,952 B1 | 8/2001 | Weisburg et al. |
| 6,326,486 B1 | 12/2001 | Hogan et al. |
| 6,350,579 B1 | 2/2002 | Nelson |
| 6,361,945 B1 | 3/2002 | Becker et al. |
| 6,534,273 B2 | 3/2003 | Weisburg et al. |
| 6,534,274 B2 | 3/2003 | Becker et al. |
| 6,583,275 B1 * | 6/2003 | Doucette-Stamm et al. ............. 536/23.1 |
| 6,593,114 B1 | 7/2003 | Kunsch et al. |
| 6,737,248 B2 | 5/2004 | Kunsch et al. |
| 6,835,542 B2 | 12/2004 | Becker et al. |
| 6,849,412 B2 | 2/2005 | Becker et al. |
| 6,949,367 B1 | 9/2005 | Dempcy et al. |
| 2006/0046265 A1 | 3/2006 | Becker et al. |
| 2006/0068417 A1 | 3/2006 | Becker et al. |
| 2006/0194240 A1 | 8/2006 | Arnold, Jr. et al. |

FOREIGN PATENT DOCUMENTS

| | | | |
|---|---|---|---|
| WO | 8801302 A1 | 2/1988 |
| WO | 8810315 A1 | 12/1988 |
| WO | 9313121 A1 | 7/1993 |
| WO | 9503430 A1 | 2/1995 |
| WO | 0066789 A2 | 11/2000 |
| WO | WO 01/40521 | 6/2001 |
| WO | WO 02/34771 | 5/2002 |
| WO | 2004046375 A2 | 6/2004 |

(Continued)

OTHER PUBLICATIONS

Ferguson et al., "Bacteriological Monitoring Studies to Identify Sources of Fecal Pollution at Baby Beach, Dana Point Harbor, California," Abstract #738, 3 pages, Orange County Public Health Laboratory, Newport Beach, CA, USA.

McKinney, Julie Michelle, Master's Thesis defended on Apr. 28, 2004, Virginia Polytechnic Institute and State University, "Identifying Sources of Fecal Pollution in the Appomattox River Watershed," Chapter II, pp. 9-18, Virginia, USA.

(Continued)

*Primary Examiner*—Diana B Johannsen
(74) *Attorney, Agent, or Firm*—Heather M. Osborne

(57) ABSTRACT

The disclosed invention includes nucleic acid oligomers that may be used as amplification oligomers, including primers, capture probes for sample preparation, and detection probes for detection of indicator enterococci 23S rRNA sequences in samples by using methods of specific nucleic acid amplification and detection.

18 Claims, No Drawings

OTHER PUBLICATIONS

Sinton et al., "Distinguishing human from animal faecal contamination in water: a review," New Zealand J. of Marine and Freshwater Res., 1998, pp. 323-348, vol. 32, The Royal Society of New Zealand, Wellington, New Zealand.

Ferguson et al., "Occurance of *Enterococci* in Ocean Water, Sediments, Storm Drains, Soil and Seagulls at Baby Beach, Dana Point Harbor, California," Poster #381, Orange County Public Health Laboratory, Newport Beach, CA, USA.

Ferguson et al., "Bacteriological Monitoring Studies to Identify Sources of Fecal Pollution at Baby Beach, Dana Point Harbor, California," Abstract #738, 3 pages, Orange County Public Health Laboratory, Newport Beach, CA, USA, 2003.

Quednau et al., "Genomic Relationships between *Enterococcus faecium* Strains from Different Sources and with Different Antibiotic Resistance Profiles Evaluated by Restriction Endonuclease Analysis of Total Chromosomal DNA Using EcoRI and Pvull," Appl. Environ. Microbiol., Apr. 1999, pp. 1777-1780, vol. 65, No. 4, American Society for Microbiology, Washington, D.C., USA.

Schiff et al., "Tracking sources of bacterial contamination in stormwater discharges to Mission Bay, California," Water Environment Research, Sep.-Oct. 2001, pp. 534-542, vol. 73, No. 5, Westminister, CA.

Ludwig et al., "How Quantitative is Quantitative PCR with Respect to Cell Counts?" System. Appl. Microbiol., 2000, pp. 556-562, vol. 23, Urban & Fischer Verlag, Freising, Germany.

Gen-Probe Incorporated, AccuProbe *Enterococcus* Culture Identification Test, Package Insert, Nov. 2, 2001, pp. 1-4, San Diego, CA, USA.

Wheeler et al., "Potential of *Enterococcus faecalis* as a Human Fecal Indicator for Microbial Source Tracking," J. of Environ. Qual., 2002, pp. 1286-1293, vol. 31, Madison, WI, USA.

Scott et al., "Microbial Source Tracking: Current Methodoly and Future Directions," Appl. Environ. Microbiol., Dec. 2002, pp. 5796-5803, vol. 68, No. 12, American Society for Microbiology, Washington, D.C., USA.

Frahm et al., "Application of the fluorogenic probe technique (TaqMan PCR) to the detection of *Enterococcus* spp. and *Escherichia coli* in water samples," J. Microbiol. Methods, 2003, pp. 123-131, vol. 52, Elsevier Science B.V., Germany.

Haughland et al., "Comparison of *Enterococcus* measurements in freshwater at two recreational beaches by quantitative polymerase chain reaction and membrane filter culture analysis," Water Research, 2005, vol. 39, pp. 559-568, Elsevier Ltd., Germany.

Scott et al., "Potential Use of a Host Associated Molecular Marker in *Enterococcus faecium* as an Index of Human Fecal Pollution," Environ. Sci. Technol., January 2005, pp. 283-287, vol. 39, No. 1, American Chemical Society, Gainesville, FL, USA.

He et al., "Quantification of *Enterococci* and Human Adenoviruses in Environmental Samples by Real-Time PCR," Appl. Environ. Microbiol., May 2005, pp. 2250-2255, vol. 71, No. 5, American Society for Microbiology, Washington, D.C., USA.

Ahmed et al., "Host Species-Specific Metabolic Fingerprint Database for *Enterococci* and *Escherichia coli* and Its Application to Identify Sources of Fecal Contamination in Surface Waters," Appl. Environ. Microbiol., Aug. 2005, pp. 4461-4468, vol. 71, No. 8, American Society for Microbiology, Washington, D.C., USA.

Griffith et al., "Evaluation of Rapid Microbiological Methods for Measuring Recreational Water Quality," Technical Report #485, May-Jun. 2006, pp. 1-78, Southern California Coastal Water Research Project, Westminster, CA.

Noble et al., "Multitiered Approach Using Quantitative PCR to Track Sources of Fecal Pollution Affecting Santa Monica Bay, California," Appl. Environ. Microbiol., Feb. 2006, pp. 1604-1612, vol. 72, No. 2, American Society for Microbiology, Washington, D.C., USA.

Tyagi et al., "Multicolor molecular beacons for allele discrimination," Nature Biotechnol., Jan. 1998, pp. 49-53, vol. 16, Nature Publishing Group, New York, USA.

* cited by examiner

COMPOSITIONS AND METHODS TO DETECT *ENTEROCOCCI* NUCLEIC ACID

RELATED APPLICATION

This application claims the benefit of U.S. Provisional Application No. 60/800,116, filed May 12, 2006. The entire disclosure of this prior application is hereby incorporated by reference.

FIELD OF THE INVENTION

This invention relates to detection of the presence of bacteria in a sample by using molecular biological methods, and specifically relates to detection of enterococci in a sample by amplifying nucleic acids from enterococci and detecting the amplified nucleic acid sequences.

BACKGROUND

*Enterococcus* species are members of the normal flora of the gastrointestinal tract in humans and animals and have emerged as a leading cause of nosocomial infection. The two major pathogenic species in humans are *Enterococcus faecalis* (*E. faecalis*) and *E. faecium*, with occasional infections being caused by *E. durans, E. gallinarum, E. casseliflavus, E. avium, E. hirae, E. mundtii,* and *E. raffinosus*. Enterococcal infections are particularly troublesome because of the high level of intrinsic antibiotic resistance.

Enterococci are routinely used as indicator organisms to assess the quality of recreational waters. Elevated concentrations of enterococci, particularly *E. faecalis, E. faecium* and *E. durans,* are indicative of fecal contamination and the presence of enteric pathogens. Rapid detection of enterococci in the environment is of importance in reducing the spread of multiresistant enterococci and also in assessing the quality of recreational waters.

Conventional methods for *Enterococcus* detection based on cultivation often require 1 to 2 days. Such methods are further hampered by growing bacteria in artificial media that contributes to the poor culturability of injured and stressed organisms as well as the ability of enterococci to enter a viable but nonculturable state.

The methods and compositions described herein, based on the detection of specific rRNA sequences unique to *Enterococcus* species indicative of fecal contamination (hereinafter "indicator enterococci"), allow rapid, sensitive, and specific detection of *E. faecalis, E. faecium, E. casseliflavus, E. gallinarum, E. mundtii, E. durans, E. hirae,* and *E. columbae* without detection of *E. avium, E. malodoratus, E. pseudoavium, E. raffinosus, E. saccharolyticus,* and *E. dispar.*

SUMMARY

The invention includes methods of detecting indicator enterococci in a sample, including environmental samples or biological specimens. The invention also includes nucleic acid oligomers that may be used as primers and probes for detecting indicator enterococci, which may be provided in kits. Using the specific primers and probes, the methods include the steps of amplifying target sequences in 23S rRNA sequences of indicator enterococci and detecting the amplification products. Some embodiments of the methods monitor the development of specific amplification products during the amplification step. Some embodiments of the methods also include generation of a standard curve using known amounts of 23S rRNA or detection of an internal control or calibrator sequence, which may be a non-enterococci sequence, in the assay.

One aspect of the invention includes methods of quantifying indicator enterococci in a sample by using an amplification and detection method that determines the quantity of 23S rRNA sequences of indicator enterococci nucleic acid present in a sample. Preferred embodiments include generation of a standard curve or detection of an internal control or calibrator sequence in the assay.

Another aspect of the invention includes compositions for detecting and/or quantifying indicator enterococci in a sample. Preferred embodiments include combinations of nucleic acid oligomers that function as amplification oligonucleotides in nucleic acid amplification reactions, and probes that hybridize specifically to amplified nucleic acid products. Some embodiments are kits that contain such amplification oligonucleotides and/or probes specific for indicator enterococci, which may optionally include other reagents used in nucleic acid amplification and/or detection.

DETAILED DESCRIPTION

The present invention provides methods for detecting the presence or absence of indicator enterococci in a sample, such as an environmental or biological sample. These methods provide for the sensitive and specific detection of indicator enterococci nucleic acids. The methods include performing a nucleic acid amplification of 23S rRNA sequences and detecting the amplified product, for example by specifically hybridizing the amplified product with a nucleic acid probe that provides a signal to indicate the presence of indicator enterococci in the sample. The amplification step includes contacting the sample with one or more amplification oligomers specific for a target sequence in 23S rRNA to produce an amplified product if indicator enterococci rRNA is present in the sample. Amplification synthesizes additional copies of the target sequence or its complement by using at least one nucleic acid polymerase to extend the sequence from an amplification oligomer (a primer) using a template strand. Preferred embodiments for detecting the amplified product use a hybridization step that includes contacting the amplified product with at least one probe specific for a sequence amplified by the selected amplification oligomers, e.g., a sequence contained in the target sequence flanked by a pair of selected primers. The detecting step may be performed after the amplification reaction is completed, or may be performed simultaneous with amplifying the target region, i.e., in real-time. Preferably, the detecting step that uses a probe for detection of the amplified product allows homogeneous detection, i.e., detection of the hybridized probe without removal of unhybridized probe from the mixture (e.g., U.S. Pat. Nos. 5,639,604 and 5,283,174, Arnold Jr. et al.). In preferred embodiments that detect the amplified product near or at the end of the amplification step, a linear probe is used to provide a signal to indicate hybridization of the probe to the amplified product. In other preferred embodiments that use real-time detection, the probe is preferably a hairpin probe, such as a molecular beacon, molecular torch, or hybridization switch probe, that is labeled with a reporter moiety that is detected when the probe binds to amplified product. For example, a hairpin probe may include a label, such as a fluorophore ("F"), attached to one end of the probe and an interacting compound, such as quencher ("Q"), attached to the other end of the hairpin structure to inhibit signal production from the label when the hairpin structure is in the "closed" conformation and not hybridized to the amplified product, whereas the signal is detectable when the probe is in the "open" conformation because it is hybridized to a complementary sequence in the amplified product. Various forms of such probes have been described previously (e.g., U.S. Pat. Nos. 5,118,801 and 5,312,728, Lizardi et al., U.S. Pat. Nos. 5,925,517 and 6,150,097, Tyagi et al., U.S. Pat. Nos. 6,849,412, 6,835,542, 6,534,274, and 6,361,945, Becker et al., US Pub. No. 2006-0068417, and Arnold Jr., U.S. Ser. No. 60/657,523, the details of which are hereby incorporated by reference herein).

To aid in understanding aspects of the invention, some terms used herein are described in more detail. All other scientific and technical terms used herein have the same meaning as commonly understood by those skilled in the relevant art, such as may be provided in *Dictionary of Microbiology and Molecular Biology,* 2nd ed. (Singleton et al., 1994, John Wiley & Sons, New York, N.Y.), *The Harper Collins Dictionary of Biology* (Hale & Marham, 1991, Harper Perennial, New York, N.Y.), and other references cited herein. Unless mentioned otherwise, the techniques employed or contemplated herein are standard methods well known to a person of ordinary skill in the art of molecular biology.

"Sample" includes any specimen that may contain enterococci bacteria or components thereof, such as nucleic acids or fragments of nucleic acids. Samples may be obtained from environmental sources, e.g., water, soil, slurries, debris, biofilms from containers of aqueous fluids, airborne particles or aerosols, and the like, which may include processed samples, such as obtained from passing samples over or through a filtering device, or following centrifugation, or by adherence to a medium, matrix, or support. Samples also include "biological samples" which include any tissue or material derived from a living or dead human which may contain enterococci or target nucleic acid derived therefrom, including, e.g., gastrointestinal tissue, feces, urine, or other body fluids or materials. A sample may be treated to physically or mechanically disrupt aggregates or cells therein, thus releasing intracellular components, including nucleic acids, into a solution which may contain other components, such as enzymes, buffers, salts, detergents and the like.

"Nucleic acid" refers to a multimeric compound comprising nucleotides or nucleotide analogs which have nitrogenous heterocyclic bases, or base analogs, where the nucleotides are linked together by phosphodiester bonds or other linkages to form a polynucleotide. Nucleic acids include RNA, DNA, or chimeric DNA-RNA polymers or oligomers, and analogs thereof. A nucleic acid "backbone" may be made up of a variety of linkages, including one or more of sugar-phosphodiester linkages, peptide-nucleic acid bonds ("peptide nucleic acids" or PNAs, see PCT No. WO 95/32305), phosphorothioate linkages, methylphosphonate linkages, or combinations thereof. Sugar moieties of the nucleic acid may be either ribose or deoxyribose, or similar compounds having known substitutions, e.g., 2' methoxy substitutions and 2' halide substitutions (e.g., 2'-F). Nitrogenous bases may be conventional bases (A, G, C, T, U), analogs thereof (e.g., inosine; *The Biochemistry of the Nucleic Acids* 5-36, Adams et al., ed., 11$^{th}$ ed., 1992), derivatives of purine or pyrimidine bases (e.g., $N^4$-methyl deoxyguanosine, deaza- or aza-purines, deaza- or aza-pyrimidines, pyrimidine bases having substituent groups at the 5 or 6 position, purine bases having an altered or replacement substituent at the 2, 6 and/or 8 position, such as 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines, and pyrazolo-compounds, such as unsubstituted or 3-substituted pyrazolo[3,4-d]pyrimidine; U.S. Pat. Nos. 5,378,825, 6,949,367 and PCT No. WO 93/13121). Nucleic acids may include "abasic" residues in which the backbone does not include a nitrogenous base for one or more residues (U.S. Pat. No. 5,585,481, Arnold et al.). A nucleic acid may comprise only conventional sugars, bases, and linkages as found in RNA and DNA, or may include conventional components and substitutions (e.g., conventional bases linked by a 2' methoxy backbone, or a nucleic acid including a mixture of conventional bases and one or more base analogs). Nucleic acids also include "locked nucleic acids" (LNA), an analogue containing one or more LNA nucleotide monomers with a bicyclic furanose unit locked in an RNA mimicking sugar conformation, which enhances hybridization affinity toward complementary sequences in single-stranded RNA (ssRNA), single-stranded DNA (ssDNA), or double-stranded DNA (dsDNA) (Vester et al., 2004, *Biochemistry* 43(42): 13233-41). Synthetic methods for making nucleic acids in vitro are well known in the art.

The interchangeable terms "oligomer" and "oligonucleotide" refer to a nucleic acid having generally less than 1,000 residues, including polymers in a range having a lower limit of about 2 to 5 nt residues and an upper limit of about 500 to 900 nt residues. Preferred oligomers are in a size range having a lower limit of about 5 to 15 nt and an upper limit of about 50 to 600 nt, and particularly preferred embodiments are in a range having a lower limit of about 10 to 20 nt and an upper limit of about 22 to 100 nt. Oligomers may be purified from naturally occurring sources, but preferably are synthesized using any of a variety of well-known enzymatic or chemical methods.

An "amplification oligomer" is an oligomer that hybridizes to a target nucleic acid, or its complement, and participates in a nucleic acid amplification reaction. An example of an amplification oligomer is a "primer" that hybridizes to a template nucleic acid and contains a 3' OH end that is extended by a polymerase in an amplification process. Another example of an amplification oligomer is an oligomer that is not extended by a polymerase (e.g., because it has a 3' blocked end) but participates in or facilitates amplification. Preferred size ranges for amplification oligomers include those that are about 10 to about 60 nt long and contain at least about 10 contiguous bases, and more preferably at least 12 contiguous bases that are complementary to a region of the target nucleic acid sequence (or a complementary strand thereof). The contiguous bases are preferably at least 80%, more preferably at least 90%, and most preferably about 100% complementary to the target sequence to which the amplification oligomer binds. An amplification oligomer may optionally include modified nucleotides or analogs, or additional nucleotides that participate in an amplification reaction but are not complementary to or contained in the target nucleic acid. An amplification oligomer may contain a sequence that is not complementary to the target or template sequence. For example, the 5' region of a primer may include a promoter sequence that is non-complementary to the target nucleic acid (referred to as a "promoter-primer"). Those skilled in the art will understand that an amplification oligomer that functions as a primer may be modified to include a 5' promoter sequence, and thus function as a promoter-primer. Similarly, a promoter-primer may be modified by removal of, or synthesis without, a promoter sequence and still function as a primer. A 3' blocked amplification oligomer may provide a promoter sequence and serve as a template for polymerization (referred to as a "promoter-provider").

"Amplification" refers to any known procedure for obtaining multiple copies of a target nucleic acid sequence or its complement or fragments thereof. Amplification of "fragments" refers to production of an amplified nucleic acid that contains less than the complete target nucleic acid or its complement, e.g., produced by using an amplification oligonucleotide that hybridizes to, and initiates polymerization from, an internal position of the target nucleic acid. Known amplification methods include, for example, replicase-mediated amplification, polymerase chain reaction (PCR), ligase chain reaction (LCR), strand-displacement amplification (SDA), and transcription-mediated or transcription-associated amplification. Replicase-mediated amplification uses self-replicating RNA molecules and a replicase such as QB-replicase (e.g., U.S. Pat. No. 4,786,600, Kramer et al.). PCR amplification uses a DNA polymerase, pairs of primers, and thermal cycling to synthesize multiple copies of two complementary strands of dsDNA or from a cDNA (e.g., U.S. Pat. Nos. 4,683,195, 4,683,202, and 4,800,159, Mullis et al.). LCR amplification uses four or more different oligonucleotides to amplify a target and its complementary strand by using multiple cycles of hybridization, ligation, and denaturation (e.g., U.S. Pat. No. 5,427,930, Birkenmeyer et al., U.S. Pat. No. 5,516,663, Backman et al.). SDA uses a primer that contains a recognition site for a restriction endonuclease and an endonuclease that nicks one strand of a hemimodified DNA duplex that includes the target sequence, whereby amplification occurs in a series of primer extension and strand displacement steps (e.g., U.S. Pat. No. 5,422,252, Walker et al., U.S. Pat. No. 5,547,861, Nadeau et al., U.S. Pat. No. 5,648,211, Fraiser et al.).

"Transcription-associated amplification" or "transcription-mediated amplification" (TMA) refers to any type of nucleic acid amplification that uses an RNA polymerase to produce multiple RNA transcripts from a nucleic acid template. These methods generally employ an RNA polymerase, a DNA polymerase, deoxyribonucleoside triphosphates, ribonucleoside triphosphates, and a template complementary oligonucleotide that includes a promoter sequence, and optionally may include one or more other oligonucleotides. Variations of transcription-associated amplification are well known in the art as disclosed in detail previously (U.S. Pat. Nos. 5,399,491 and 5,554,516, Kacian et al.; U.S. Pat. No. 5,437,990, Burg et al.; PCT Nos. WO 88/01302 and WO 88/10315, Gingeras et al.; U.S. Pat. No. 5,130,238, Malek et al.; U.S. Pat. Nos. 4,868,105 and 5,124,246, Urdea et al.; PCT No. WO 95/03430, Ryder et al.; and US Pub. No. 2006-0046265, Becker et al.). The TMA methods of Kacian et al. and the one-primer transcription-associated method of Becker et al. are preferred embodiments of amplification methods used for detection of indicator enterococci target sequences as described below. Although preferred embodiments are illustrated by using TMA or transcription-associated amplification, a person of ordinary skill in the art will appreciated that amplification oligomers disclosed herein may be readily applicable to use in other amplification methods based on extension of oligomer sequences by a polymerase.

"Probe" refers to a nucleic acid oligomer that hybridizes specifically to a target sequence in a nucleic acid, preferably in an amplified nucleic acid, under conditions that promote hybridization to allow detection of the target sequence or amplified nucleic acid. Detection may either be direct (i.e., a probe hybridized directly to its target sequence) or indirect (i.e., a probe linked to its target via an intermediate molecular structure). A probe's "target sequence" generally refers to a sequence within a larger sequence (e.g., a subset of an amplified sequence) that hybridizes specifically to at least a portion of a probe oligomer by standard base pairing. A probe may comprise target-specific sequences and other sequences that contribute to the three-dimensional conformation of the probe (e.g., as described in U.S. Pat. Nos. 5,118,801 and 5,312,728, Lizardi et al.; and U.S. Pat. Nos. 6,849,412, 6,835,542, 6,534,274 and 6,361,945, Becker et al., US Pub. No. 2006-0068417, Becker et al.).

By "sufficiently complementary" is meant a contiguous sequence that is capable of hybridizing to another sequence by hydrogen bonding between a series of complementary bases, which may be complementary at each position in the sequence by standard base pairing (e.g., G:C, A:T or A:U pairing) or may contain one or more residues, including abasic residues, that are not complementary by standard hydrogen bonding. Contiguous bases are at least 80%, preferably at least 90%, and more preferably about 100% complementary to a sequence to which an oligomer is intended to specifically hybridize. Sequences that are "sufficiently complementary" allow stable hybridization of a nucleic acid oligomer to its target sequence under the selected hybridization conditions, even if the sequences are not completely complementary. Appropriate hybridization conditions are well-known in the art, can be predicted readily based on base sequence composition, or can be determined by using routine testing (e.g., Sambrook et al., *Molecular Cloning, A Laboratory Manual*, $2^{nd}$ ed. (Cold Spring Harbor Laboratory Press, Cold Spring Harbor, N.Y., 1989) at §§ 1.90-1.91, 7.37-7.57, 9.47-9.51 and 11.47-11.57 particularly at §§ 9.50-9.51, 11.12-11.13, 11.45-11.47 and 11.55-11.57).

"Sample preparation" refers to any steps or method that prepares a sample for subsequent amplification and detection of enterococci nucleic acids present in the sample. Sample preparation may include any known method of concentrating components from a larger sample volume or from a substantially aqueous mixture, such as by filtration of airborne particles from an air sample or microbes from an environmental water sample. Sample preparation may include lysis of cellular components and removal of debris, such as by filtration or centrifugation. Sample preparation may include use of nucleic acid oligomers that selectively capture a target nucleic acid from other sample components.

A "capture probe" or "capture oligomer" refers to at least one nucleic acid oligomer that joins a target sequence and an immobilized oligomer by using base pair hybridization. A preferred embodiment of a capture oligomer includes two binding regions: a target sequence-binding region and an immobilized probe-binding region, usually on the same oligomer, although the two regions may be present on different oligomers that are joined by one or more linkers. For example, a first oligomer may include the immobilized probe-binding region and a second oligomer may include the target sequence-binding region, and the two different oligomers are joined by hydrogen bonding with a linker that links the two sequences of the first and second oligomers.

An "immobilized probe" or "immobilized nucleic acid" refers to a nucleic acid that joins, directly or indirectly, a capture oligomer to an immobilized support. A preferred immobilized probe is an oligomer joined to a solid support that facilitates separation of bound target sequence from unbound material in a sample. Solid supports may include known materials, such as matrices and particles free in solution, e.g., such materials made up of nitrocellulose, nylon, glass, polyacrylate, mixed polymers, polystyrene, silane, polypropylene, metal and preferred embodiments are magnetically attractable particles. Preferred supports are monodisperse magnetic spheres (e.g., uniform size ±5%, to provide consistent results), to which an immobilized probe is joined directly (via covalent linkage, chelation, or ionic interaction), or indirectly (via one or more linkers), where the linkage or interaction between the probe and support is stable during hybridization conditions.

"Separating" or "purifying" means that one or more components of a sample are removed or separated from one or more other sample components. Sample components include target nucleic acids in a generally aqueous solution phase that may also include cellular fragments, proteins, carbohydrates, lipids, and other nucleic acids. Separating or purifying removes at least 70%, preferably at least 80%, and more preferably about 95% of the target nucleic acid from other sample components.

A "label" refers to a molecular moiety or compound that can be detected or lead to a detectable response. A label may be joined directly or indirectly to a nucleic acid probe. Direct labeling can occur through bonds or interactions that link the label to the probe, including covalent bonds or non-covalent interactions, e.g. hydrogen bonds, hydrophobic and ionic interactions, or formation of chelates or coordination complexes. Indirect labeling can occur through use of a bridging moiety or "linker" such as an antibody or additional oligomer, which is either directly or indirectly labeled, and which may amplify the detectable signal. Labels include any detectable moiety, such as a radionuclide, ligand (e.g., biotin, avidin), enzyme or enzyme substrate, reactive group, or chromophore (e.g., dye, particle, or bead that imparts detectable color), luminescent compound (e.g., bioluminescent, phosphorescent, or chemiluminescent labels), or fluorophore. Preferred labels are detectable in a homogeneous assay in which bound labeled probe in a mixture exhibits a detectable change that is different when compared to unbound labeled probe, e.g., stability or differential degradation. A "homogeneous detectable label" can be detected without physically removing hybridized bound from unbound forms of the label or labeled probe (described in U.S. Pat. No. 5,283,174, Arnold et al.; U.S. Pat. No. 5,656,207, Woodhead et al.; and U.S. Pat. No. 5,658,737, Nelson et al.). Preferred labels include chemiluminescent compounds, more preferably acridinium ester ("AE") compounds that include standard AE and derivatives thereof (described in U.S. Pat. No. 5,656,207, Woodhead et al.; U.S. Pat. No. 5,658,737, Nelson et al.; U.S. Pat. No. 5,639,604, Arnold, Jr., et al.) or fluorophores, more preferably fluorescein in conjunction with a DABCYL quencher or ROX in conjunction with a TAMRA quencher. Synthesis and methods of attaching labels to nucleic acids and detecting labels are well known (e.g., Sambrook et al., *Molecular Cloning, A Laboratory Manual*, 2nd ed. (Cold Spring Harbor Laboratory Press, Cold Spring Habor, N.Y., 1989), Chapter 10; U.S. Pat. No. 5,658,737, Nelson et al.; U.S. Pat. No. 5,656,207, Woodhead et al.; U.S. Pat. No. 5,547,842, Hogan et al.; U.S. Pat. No. 5,283,174, Arnold et al.; U.S. Pat. No. 4,581,333, Kourilsky et al.).

The invention includes methods of amplifying and detecting indicator enterococci nucleic acid, specifically sequences of indicator enterococci 23S rRNA or genes encoding 23S rRNA. The invention includes oligonucleotide sequences that specifically recognize target sequences of indicator enterococci 23S rRNA or their complementary sequences, or genes encoding 23S rRNA or their complementary sequences. Such oligonucleotide sequences may be used as amplification oligomers, which may include primers, promoter-primers, blocked oligomers, and promoter-provider oligomers, whose functions have been generally described previously (e.g., U.S. Pat. Nos. 5,399,491, 5,554,516 and 5,824,518, Kacian et al.; and US Pub. No. 2006-0046265, Becker et al., and U.S. Pat. Nos. 4,683,195, 4,683,202, and 4,800,159, Mullis et al.). Other embodiments of the oligonucleotide sequences may be used as probes for detecting amplified sequences of indicator enterococci.

Amplification methods that use TMA amplification include the following steps (described previously in U.S. Pat. Nos. 5,399,491, 5,554,516 and 5,824,518, Kacian et al., the details of which are incorporated by reference herein). Briefly, the target nucleic acid that contains the sequence to be amplified is provided as single-stranded nucleic acid (e.g., ssRNA or ssDNA). Those skilled in the art will appreciate that conventional melting of double-stranded nucleic acid (e.g., dsDNA) may be used to provide single-stranded target nucleic acids. A promoter-primer binds specifically to the target nucleic acid at its target sequence and a reverse transcriptase (RT) extends the 3' end of the promoter-primer using the target strand as a template to create a cDNA copy of the target sequence strand, resulting in an RNA:DNA duplex. RNase (e.g., RNaseH of the RT) digests the RNA strand of the RNA:DNA duplex and a second primer binds specifically to its target sequence which is located on the cDNA strand downstream from the promoter-primer end. RT synthesizes a new DNA strand by extending the 3' end of the second primer using the first cDNA template to create a dsDNA that contains a functional promoter sequence. An RNA polymerase specific for the promoter sequence then initiates transcription to produce RNA transcripts that are about 100 to 1000 amplified copies ("amplicons") of the initial target strand in the reaction. Amplification continues when the second primer binds specifically to its target sequence in each of the amplicons and RT creates a DNA copy from the amplicon RNA template to produce an RNA:DNA duplex. RNase in the reaction mixture digests the amplicon RNA from the RNA:DNA duplex and the promoter primer binds specifically to its complementary sequence in the newly synthesized DNA. RT extends the 3' end of the promoter primer to create a dsDNA that contains a functional promoter to which the RNA polymerase binds to transcribe additional amplicons that are complementary to the target strand. The autocatalytic cycles of making more amplicon copies repeat during the course of the reaction resulting in about a billion-fold amplification of the target nucleic acid present in the sample. The amplified products may be detected during amplification, i.e., in real-time, or at the end of the amplification reaction by using a probe that binds specifically to a target sequence contained in the amplified products. Detection of a signal resulting from the bound probes indicates the presence of the target nucleic acid in the sample.

Another version of transcription associated amplification uses one primer and one or more additional amplification oligomers to amplify nucleic acids in vitro, making transcripts (amplicons) that indicate the presence of the target sequence in a sample (previously described in detail in US Pub. No. 2006-0046265, Becker et al., the details of which are hereby incorporated herein by reference). Briefly, the single-primer TMA method uses a primer (or "priming oligomer"), a modified promoter oligomer (or "promoter-provider") that is modified to prevent the initiation of DNA synthesis from its 3' end (e.g., by including a 3'-blocking moiety) and, optionally, a binding molecule (e.g., a 3'-blocked extender oligomer) to terminate elongation of a cDNA from the target strand. This method synthesizes multiple copies of a target sequence and includes the steps of treating a target RNA that contains a target sequence with a priming oligomer and a binding molecule, where the primer hybridizes to the 3' end of the target strand. RT initiates primer extension from the 3' end of the primer to produce a cDNA which is in a duplex with the target strand (e.g., RNA:cDNA). When a binding molecule, such as a 3' blocked extender oligomer, is used in the reaction, it binds to the target nucleic acid adjacent near the 5' end of the target sequence. That is, the binding molecule binds to the target strand next to the 5' end of the target sequence to be amplified. When the primer is extended by DNA polymerase activity of RT to produce cDNA, the 3' end of the cDNA is determined by the position of the binding molecule because polymerization stops when the primer extension product reaches the binding molecule bound to the target strand. Thus, the 3' end of the cDNA is complementary to the 5' end of the target sequence. The RNA:cDNA duplex is separated when RNase (e.g., RNase H of RT) degrades the RNA strand, although those skilled in the art will appreciate that any form of strand separation may be used. Then, the promoter-provider oligomer hybridizes to the cDNA near the 3' end of the cDNA strand. The promoter-provider oligomer includes a 5' promoter sequence for an RNA polymerase and a 3' region complementary to a sequence in the 3' region of the cDNA. The promoter-provider oligomer also has a modified 3' end that includes a blocking moiety that prevents initiation of DNA synthesis from the 3' end of the promoter-provider oligomer. In the promoter-provider:cDNA duplex, the 3'-end of the cDNA is extended by DNA polymerase activity of RT using the promoter oligomer as a template to add a promoter sequence to the cDNA and create a functional double-stranded promoter. An RNA polymerase specific for the promoter sequence then binds to the functional promoter and transcribes multiple RNA transcripts complementary to the cDNA and substantially identical to the target region sequence that was amplified from the initial target strand. The resulting amplified RNA can then cycle through the process again by binding the primer and serving as a template for further cDNA production, ultimately producing many amplicons from the initial target nucleic acid present in the sample. Some embodiments of the single-primer transcription associated amplification method do not include the binding molecule and, therefore, the cDNA product made from the primer has an indeterminate 3' end, but the amplification steps proceed substantially as described above for all other steps.

Detection of the amplified products may be accomplished by a variety of methods. The nucleic acids may be associated with a surface that results in a physical change, such as a detectable electrical change. Amplified nucleic acids may be detected by concentrating them in or on a matrix and detecting the nucleic acids or dyes associated with them (e.g., an intercalating agent such as ethidium bromide or cyber green), or detecting an increase in dye associated with nucleic acid in solution phase. Other methods of detection may use nucleic acid probes that are complementary to a sequence in the amplified product and detecting the presence of the probe: product complex, or by using a complex of probes that may amplify the detectable signal associated with the amplified products (e.g., U.S. Pat. Nos. 5,424,413 and 5,451,503, Hogan et al., U.S. Pat. No. 5,849,481, Urdea et al.). Directly or indirectly labeled probes that specifically associate with the amplified product provide a detectable signal that indicates the presence of the target nucleic acid in the sample. For example, if the target nucleic acid is indicator enterococci 23S rRNA, the amplified product will contain a target sequence in or complementary to a sequence in indicator enterococci 23S rRNA, and a probe will bind directly or indirectly to a sequence contained in the amplified product to indicate the presence of indicator enterococci in the tested sample.

Preferred embodiments of probes that hybridize to the complementary amplified sequences may be DNA or RNA oligomers, or oligomers that contain a combination of DNA and RNA nucleotides, or oligomers synthesized with a modified backbone, e.g., an oligomer that includes one or more 2'-methoxy substituted ribonucleotides. Probes used for detection of the amplified indicator enterococci rRNA sequences may be unlabeled and detected indirectly (e.g., by binding of another binding partner to a moiety on the probe) or may be labeled with a variety of detectable labels. Preferred embodiments of labels include compounds that emit a detectable light signal, e.g., fluorophores or luminescent compounds that can be detected in a homogeneous mixture. More than one label, and more than one type of label, may be present on a particular probe, or detection may rely on using a mixture of probes in which each probe is labeled with a compound that produces a detectable signal (e.g., U.S. Pat. Nos. 6,180,340 and 6,350,579, Nelson). Labels may be attached to a probe by various means including covalent linkages, chelation, and ionic interactions, but preferably the label is covalently attached. Probes may be linear oligomers that do not substantially form conformations held by intramolecular bonds or oligomers that form conformations generally referred to as hairpins by using intramolecular hybridization. Preferred embodiments of linear oligomers generally include a chemiluminescent compound as the label, preferably an AE compound.

Hairpin probes are preferably labeled with any of a variety of different types of interacting labels, where one interacting member is usually attached to the 5' end of the hairpin probe and the other interacting member is attached to the 3' end of the hairpin probe. Such interacting members, which may be generally referred to as a reporter dye and a quencher, include a luminescent/quencher pair, luminescent/adduct pair, Förster or contact energy transfer pair, or a dye dimer. A luminescent/quencher pair may be made up of one or more luminescent labels, such as chemiluminescent or fluorescent labels, and one or more quenchers. In preferred embodiments, a hairpin probe is labeled at one end with a fluorescent label ("F") that absorbs light of a particular wavelength or range and emits light another emission wavelength or range and at the other end with a quencher ("Q") that attenuates, partially or completely, signal emitted from the excited F when Q is in proximity with the fluorophore. Such a hairpin probe may be referred to as labeled with a fluorescent/quencher (F/Q) pair. Fluorophores are well known compounds that include, e.g., acridine, fluorescein, sulforhodamine 101, rhodamine, 5-(2'-aminoethyl)aminoaphthaline-1-sulfonic acid (EDANS), Texas Red, Eosine, Bodipy and lucifer yellow (Tyagi et al., Nature Biotechnology 16:49-53, 1998). Quenchers are also well known and include, e.g., 4-(4'-dimethyl-amino-phenylaxo)benzoic acid (DABCYL), thallium, cesium, and p-xylene-bis-pyridinium bromide. Different F/Q combinations are well known and many combinations may function together, e.g., DABCYL with fluorescein, rhodamine, or EDANS. Other combinations of labels for hairpin probes include a reporter dye, e.g., FAM™, TET™, JOE™, VIC™ combined with a quencher such as TAMRA™ or a non-fluorescent quencher.

A preferred embodiment of a hairpin probe is a "molecular torch" that detects an amplified product to indicate whether a target indicator enterococci sequence is present in the sample after the amplification step. A molecular torch comprises: (1) a target detection means for hybridizing to the target sequence, if present, resulting in an "open" conformation; (2) torch closing means for hybridizing to the target detecting means in the absence of the target sequence resulting in a "closed" conformation; and (3) a joining means that joins the target detection means and the torch closing means (e.g., U.S. Pat. Nos. 6,849,412, 6,835,542, 6,534,274, and 6,361,945, Becker et al., the details of which are incorporated by reference herein). The open torch conformation results in a detectable signal that indicates the presence of the amplified target sequence, whereas the closed torch conformation produces an amount of signal that is distinguishable from that of the open conformation. Another preferred hairpin probe embodiment is a "molecular beacon" that includes a label on one arm of the hairpin sequence, a quencher on the other arm, and a loop region joining the two arms (U.S. Pat. Nos. 5,118,801 and 5,312,728, Lizardi et al., the details of which are incorporated by reference herein). Methods for using such hairpin probes are well known in the art.

Oligomers that are not intended to be extended by a nucleic acid polymerase preferably include a blocker group that replaces the 3' OH to prevent enzyme-mediated extension of the oligomer in an amplification reaction. For example, blocked amplification oligomers and/or detection probes present during amplification preferably do not have a functional 3' OH and instead include one or more blocking groups located at or near the 3' end. A blocking group near the 3' end is preferably within five residues of the 3' end and is sufficiently large to limit binding of a polymerase to the oligomer, and other preferred embodiments contain a blocking group covalently attached to the 3' terminus. Many different chemical groups may be used to block the 3' end, e.g., alkyl groups, non-nucleotide linkers, alkane-diol dideoxynucleotide residues, and cordycepin.

A preferred method for detection of indicator enterococci sequences uses a transcription-associated amplification with a hairpin probe, e.g. molecular torch or molecular beacon, because the probe may be added before amplification, and detection carried out without addition of other reagents. For example, a probe may be designed so that the melting temperature ($T_m$) of the hybridized arms of the hairpin probe (e.g., target binding domain:target closing domain complex of a molecular torch) is higher than the amplification reaction temperature to prevent the probe from prematurely binding to amplified target sequences. After an interval of amplification, the mixture is heated to open the torch probe arms and allow the target binding domain to hybridize to its target sequence in the amplified product. The solution is then cooled to close probes not bound to amplified products, which closes the label/quencher (e.g., F/Q) pair, allowing detection of signals from probes hybridized to the amplified target sequences in a homogeneous manner. For example, with an F/Q labeled hairpin probe, the mixture is irradiated with the appropriate excitation light and the emission signal is measured.

In other embodiments, the hairpin detection probe is designed so that the amplified products preferentially hybridize to the target binding domain of the probe during amplification, resulting in changing the hairpin to its "open" conformation as amplification progresses, and the amplification reaction mixture is irradiated at intervals during the amplification reaction to detect the emitted signal from the open probes in real-time during amplification.

Preparation of samples for amplification and detection of indicator enterococci sequences may include methods of separating and/or concentrating organisms contained in a sample from other sample components, e.g., filtration of particulate matter from air, water or other types of samples. Sample preparation may also include routine methods of disrupting cells or lysing bacteria to release intracellular contents, including indicator enterococci 23S rRNA or genetic sequences encoding 23S rRNA. Sample preparation before amplification may further include an optional step of target capture to specifically or non-specifically separate the target nucleic acids from other sample components. Nonspecific target capture methods may involve selective precipitation of nucleic acids from a substantially aqueous mixture, adherence of nucleic acids to a support that is washed to remove other sample components, or other means of physically separating nucleic acids from a mixture that contains indicator enterococci nucleic acid and other sample components.

In a preferred embodiment, indicator enterococci rRNA or genes encoding rRNA are selectively separated from other sample components by specifically hybridizing the indicator enterococci nucleic acid to a capture oligomer specific for the indicator enterococci target sequence to form a target sequence:capture probe complex that is separated from sample components. A preferred method of specific target capture binds the indicator enterococci target:capture probe complex to an immobilized probe to form a target:capture probe:immobilized probe complex that is separated from the sample and, optionally, washed to remove non-target sample components, as previously described (U.S. Pat. Nos. 6,110, 678, 6,280,952, and 6,534,273, Weisburg et al., the details of which are incorporated by reference herein). Briefly, the capture probe oligomer includes a sequence that specifically binds to the indicator enterococci target sequence in 23S rRNA or in a gene encoding 23S rRNA and also includes a specific binding partner that attaches the capture probe with its bound target sequence to a solid support, to facilitate separating the target sequence from the sample components. In a preferred embodiment, the specific binding partner of the capture probe is a 3' "tail" sequence that is not complementary to the indicator enterococci target sequence but that hybridizes to a complementary sequence on an immobilized probe attached to a solid support. Any sequence may be used in a tail region, which is generally about 5 to 50 nt long, and preferred embodiments include a substantially homopolymeric tail of about 10 to 40 nt (e.g., $A_{10}$ to $A_{40}$), more preferably about 14 to 33 nt (e.g., $A_{14}$ to $A_{30}$ or $T_3A_{14}$ to $T_3A_{30}$), that bind to a complementary immobilized sequence (e.g., poly-T) attached to a solid support, e.g., a matrix or particle. Target capture preferably occurs in a solution phase mixture that contains one or more capture oligomers that hybridize specifically to indicator enterococci rRNA or gene target sequence under hybridizing conditions, usually at a temperature higher than the $T_m$ of the tail sequence:immobilized probe sequence duplex. Then, the indicator enterococci target:capture probe complex is captured by adjusting the hybridization conditions so that the capture probe tail hybridizes to the immobilized probe, and the entire complex on the solid support is then separated from other sample components. The support with the attached immobilized probe:capture probe: indicator enterococci target sequence may be washed one or more times to further remove other sample components. Preferred embodiments use a particulate solid support, such as paramagnetic beads, so that particles with the attached indicator enterococci target:capture probe:immobilized probe complex may be suspended in a washing solution and retrieved from the washing solution, preferably by using magnetic attraction. The enterococci target nucleic acid is eluted by dissociation of the complex in water, low ionic strength buffer, buffer containing chaotropic species and/or by application of heat. Alternatively, to limit the number of handling steps, the indicator enterococci target nucleic acid may be amplified by simply mixing the indicator enterococci target sequence in the complex on the support with amplification oligomers and proceeding with amplification steps.

Assays for detection of indicator enterococci nucleic acid may optionally include a non-enterococci internal control (IC) nucleic acid that is amplified and detected in the same assay reaction mixtures by using amplification and detection oligomers specific for the IC sequence. Amplification and detection of a signal from the amplified IC sequence demonstrates that the assay reagents, conditions, and performance of assay steps were properly used in the assay if no signal is obtained for the intended target indicator enterococci nucleic acid (e.g., samples that test negative for indicator enterococci). The IC may be used as an internal calibrator for the assay when a quantitative result is desired, i.e., the signal obtained from the IC amplification and detection is used to set a parameter used in an algorithm for quantitating the amount of indicator enterococci nucleic acid in a sample based on the signal obtained for amplified an indicator enterococci target sequence. A preferred embodiment of an IC is a randomized sequence that has been derived from a naturally occurring source (e.g., an HIV sequence that has been rearranged in a random manner). A preferred IC may be an RNA transcript isolated from a naturally occurring source or synthesized in vitro, such as by making transcripts from a cloned randomized sequence such that the number of copies of IC included in an assay may be accurately determined. The primers and probe for the IC target sequence are designed and synthesized by using any well known method provided that the primers and probe function for amplification of the IC target sequence and detection of the amplified IC sequence using substantially the same assay conditions used to amplify and detect the indicator enterococci target sequence. In preferred embodiments that include a target capture-based purification step, it is preferred that a target capture probe specific for the IC target be included in the assay in the target capture step so that the IC is treated in the assay in a manner analogous to that for the intended indicator enterococci analyte in all of the assay steps.

Alternatively, a quantitative result may be achieved by amplifying and detecting known amounts of purified or synthetic enterococci nucleic acid in a similar manner to the samples. Preferably, the known and unknown samples are processed contemporaneously. In this way, the measured response of the unknown samples can be compared with that of the known amounts and a quantitative result thus obtained. In a further aspect, a quantitative result may be achieved by "calibrating" the method by determining the response of the method to known amounts of enterococci.

EXAMPLES

For amplification and detection of sequences found in the 23S rRNA sequences (which include 23S rRNA and genes encoding 23S rRNA) of indicator enterococci, oligomers were designed that act as amplification oligomers and detection probes by comparing known sequences of 23S rRNA or gene sequences encoding 23S rRNA and selecting sequences that are common to indicator enterococci isolates, but preferably are not completely shared with 23S rRNA sequences of non-indicator enterococci or other bacteria. Sequence comparisons were conducted by using known 23S rRNA sequences (rRNA or genes) of *Enterococcus* species (*E. avium, E. malodoratus, E. pseudoavium, E. raffinosus, E. saccharolyticus, E. faecalis, E. faecium, E. casseliflavus, E. gallinarum, E. mundtii, E. dispar, E. durans, E. hirae, E. asini, E. cecorum, E. sulfureus,* and *E. columbae*) and of other bacterial species (*Lactococcus lactis, Listeria monocytogenes, Staphylococcus epidermidis,* and *Streptococcus bovis*). Specific sequences were selected, synthesized in vitro, and the oligomers were characterized by determining the $T_m$ and hybridization characteristics of the indicator enterococci oligomers with complementary target sequences (synthetic or purified rRNA from bacteria) by using standard laboratory methods. Then, selected oligomer sequences were further tested by making different combinations of amplification oligomers (Table 1) in amplification reactions with synthetic 23S RNA target sequences or 23S rRNA purified from various indicator enterococci grown in culture and performing amplification reactions to determine the efficiency of amplification of the 23S rRNA target sequences. The relative efficiencies of different combinations of amplification oligomers were monitored by detecting the amplified products of the amplification reactions, generally by binding a labeled probe (Table 2) to the amplified products and detecting the relative amount of signal that indicated the amount of amplified product made.

Embodiments of amplification oligomers for indicator enterococci 23S rRNA sequences include those shown in Table 1. Amplification oligomers include those that may function as primers, promoter-primers, and promoter-provider oligomers, with promoter sequences shown in lower case in Table 1. Some embodiments are the target-specific sequence of a promoter-primer or promoter-provider oligomer listed in Table 1, which optionally may be attached to the 3' end of any known promoter sequence. An example of a promoter sequence specific for the RNA polymerase of bacteriophage T7 is SEQ ID NO: 49 (AATTTAATACGACTCACTATAGGGAGA). Embodiments of amplification oligomers may include a mixture of DNA and RNA bases or 2' methoxy linkages for the backbone joining RNA bases. Embodiments of amplification oligomers may also be modified by synthesizing the oligomer with the 3' blocked to make them optimal for use in a single-primer transcription-associated amplification reaction, i.e., functioning as blocking molecules or promoter-provider oligomers. Preferred embodiments of 3' blocked oligomers include those of SEQ ID NOS: 32, 34, 36, 38 and 40 that include a blocked C near or at the 3' end.

TABLE 1

23S rRNA Amplification Oligomers

| Sequence | SEQ ID NO. |
|---|---|
| GAGATAGCTGGTTCTCTCC | 1 |
| GAGATAGCTGGTTCTCTCCG | 2 |
| GAGATAGCTGGTTCTCTCCGA | 3 |

TABLE 1-continued 23S rRNA Amplification Oligomers

| Sequence | SEQ ID NO. |
|---|---|
| CCTAGTCCAAACAGTGCTCTAC | 4 |
| aatttaatacgactcactatagggagaCCTAGTCCAAACAGTGCTCTAC | 5 |
| CCCTAGTCCAAACAGTGCTCTACC | 6 |
| aatttaatacgactcactatagggagaCCCTAGTCCAAACAGTGCTCTACC | 7 |
| CCCTAGTCCAAACAGTGCTCTACCTC | 8 |
| aatttaatacgactcactatagggagaCCCTAGTCCAAACAGTGCTCTACCTC | 9 |
| CCTAGTCCAAACAGTGCTCTAC | 26 |
| GATGGGCCCCTAGTCCAAACAG | 27 |
| CTGAATTCGGTAACCCGAGATG | 28 |
| GGUAACCCGAGATGGGCCCCTAGTCCAAA | 29 |
| CGAGATGGGCCCCTAGTCCAAACAGTG | 30 |
| GTAGCGGAGAAATTCCAAACGAACTTGGAGATAG | 31 |
| aatttaatacgactcactatagggagaGTAGCGGAGAAATTCCAAACGAACTTGGAGATAG | 32 |
| GTAGCGGAGAAATTCCAAACGAACTTGGAGATAGCCACAA | 33 |
| aatttaatacgactcactatagggagaGTAGCGGAGAAATTCCAAACGAACTTGGAGATAGCCACAA | 34 |
| GTAGCGGAGAAATTCCAAACGAACTTGGAGATAGCTGGTTCTCTCC | 35 |
| aatttaatacgactcactatagggagaGTAGCGGAGAAATTCCAAACGAACTTGGAGATAGCTGGTTCTCTCC | 36 |
| GAGATAGCTGGTTCTCTCCGAAATAGCTTTAGG | 37 |
| aatttaatacgactcactatagggagaGAGATAGCTGGTTCTCTCCGAAATAGCTTTAGG | 38 |
| ACTTGGAGATAGCTGGTTCTCTCCGAAATAG | 39 |
| aatttaatacgactcactatagggagaACTTGGAGATAGCTGGTTCTCTCCGAAATAG | 40 |

Embodiments of detection probe oligomers for amplified products of 23S rRNA sequences or genes encoding 23S rRNA are shown in Table 2. Preferred detection probe embodiments are oligomers that can form hairpin configurations by intramolecular hybridization of the probe sequence, which include those of SEQ ID NOs: 11, 13, 15, 17, 19, 21, 23 and 25 in Table 2, with the intramolecular hybridization sequences shown in lower case. Embodiments of the hairpin probe oligomers were synthesized with a fluorescent label attached at one end of the sequence and a quencher compound attached at the other end of the sequence. Embodiments of hairpin probes may be labeled with a 5' fluorophore and a 3' quencher, for example a 5' fluorescein label and a 3' DABCYL quencher. Some embodiments of hairpin oligomers also include a non-nucleotide linker moiety at selected positions within the sequence. Examples of such embodiments include those that include an abasic 9-carbon ("C9") linker between residues 17 and 18 of SEQ ID NO: 42, between residues 16 and 17 of SEQ ID NO: 44, between residues 17 and 18 of SEQ ID NO: 46, and between residues 14 and 15 of SEQ ID NO: 48.

TABLE 2

23S rRNA Detection Probe Oligomers

| Sequence | SEQ ID NO. |
|---|---|
| CUCGGAAUUGAGAAUG | 10 |
| ccgagCUCGGAAUUGAGAAUGcucgg | 11 |
| CCUCGGAAUUGAGAAUG | 12 |
| ccgagCCUCGGAAUUGAGAAUGcucgg | 13 |
| CUCGGAAUUGAGAAUGA | 14 |
| ccgagCUCGGAAUUGAGAAUGAcucgg | 15 |
| CCUCGGAAUUGAGAAUGA | 16 |
| ccgagCCUCGGAAUUGAGAAUGAcucgg | 17 |
| CUCGGAAUUGAGAAUGAU | 18 |
| ccgagCUCGGAAUUGAGAAUGAUcucgg | 19 |
| CUCGGAAUUGAGAAUGAUG | 20 |

TABLE 2-continued 23S rRNA Detection Probe Oligomers

| Sequence | SEQ ID NO. |
|---|---|
| ccgagCUCGGAAUUGAGAAUGAUGcucgg | 21 |
| CCUCGGAAUUGAGAAUGAU | 22 |
| ccgagCCUCGGAAUUGAGAAUGAUcucgg | 23 |
| GCCUCGGAAUUGAGAAUGA | 24 |
| ccgagGCCUCGGAAUUGAGAAUGAcucgg | 25 |
| CCUCCAUCAUUCUCAA | 41 |
| cCCUCCAUCAUUCUCAAggaggg | 42 |
| CCAUCAUUCUCAAUU | 43 |
| cCCAUCAUUCUCAAUUgauggg | 44 |
| CUCAAUUCCGAGGCU | 45 |
| ccCUCAAUUCCGAGGCUgaggg | 46 |
| UCCGAGGCUAGCCC | 47 |
| cUCCGAGGCUAGCCCggag | 48 |

Embodiments of capture probe oligomers for use in sample preparation to separate indicator enterococci 23S rRNA target nucleic acids from other sample components include those that contain the target-specific sequences of SEQ ID NO: 50 (CCACCGUGCGCCCUUAUUCACUUAAC), SEQ ID NO: 51 (GAUGUUUCAGUUCUCUGCGUCUACC), and SEQ ID NO: 52 (CGCUCGCCGCUACUCAGG-GAAUCG). Preferred embodiments of the capture probes include a 3' tail region covalently attached to the target-specific sequence to serve as a binding partner that binds a hybridization complex made up of the target nucleic acid and the capture probe to an immobilized probe on a support. Preferred embodiments of capture probes that include the target-specific sequences of SEQ ID NOs: 50, 51 and 52 further include 3' tail regions made up of substantially homopolymeric sequences, such as $dT_3A_{30}$ polymers.

Reagents used in target capture, amplification and detection steps in the examples described herein generally include one or more of the following. Sample Transport Solution contained 15 mM sodium phosphate monobasic, 15 mM sodium phosphate dibasic, 1 mM EDTA, 1 mM EGTA, and 3% (w/v) lithium lauryl sulfate (LLS), at pH 6.7. Lysis Reagent 1 contained 2.61 mM succinic acid, 0.104% (v/v) TRITON™ X-100, 2.5% (w/v) sorbitol, 2 mg/mL lysozyme, 125 U/mL mutanolysin, at pH 5.0. Lysis Reagent 2 contained 0.2 M Trizma base, 1.0 M LiCl, 20 mM EDTA, 2% (w/v) LLS, at pH 7.5. Target Capture Reagent contained 3.9 mM HEPES, 1.25% (w/v) mannitol, 0.3% (w/v) trehalose, 0.06% (v/v) TRITON X-100, 1 mg/mL of paramagnetic particles (0.7-1.05µ particles, SERA-MAG™ MG-CM, Seradyn, Inc., Indianapolis, Ind.) with $(dT)_{14}$ oligomers covalently bound thereto, and 0.01 µM SEQ ID NO: 51, at pH 7.7. Wash Solution used in target capture contained 10 mM Trizma base, 0.15 M LiCl, 1 mM EDTA, and 3.67 mM LLS, at pH 7.5. Amplification reagent was a concentrated mixture that was mixed with other reaction components (e.g., sample or specimen dilution components) to produce a mixture containing 47.6 mM Na-HEPES, 12.5 mM N-acetyl-L-cysteine, 2.5% TRITON X-100, 54.8 mM KCl, 23 mM $MgCl_2$, 3 mM NaOH, 0.35 mM of each dNTP (dATP, dCTP, dGTP, dTTP), 7.06 mM rATP, 1.35 mM rCTP, 1.35 mM UTP, 8.85 mM rGTP, 0.26 mM $Na_2EDTA$, 5% (v/v) glycerol, 2.9% trehalose, 0.225% ethanol, 0.075% methylparaben, 0.015% propylparaben, and 0.002% Phenol Red, at pH 7.5-7.6. Amplification oligomers (primers, promoter-primers, blocker oligomers, promoter-provider oligomers), and optionally probes, may be added to the reaction mixture in the amplification reagent or separate from the amplification reagent. Enzymes were added to TMA reaction mixtures at about 90 U/µL of MMLV reverse transcriptase (RT) and about 20 U/µL of T7 RNA polymerase per reaction (1 U of RT incorporates 1 nmol of dTTP in 10 min at 37° C. using 200-400 micromolar oligo dT-primed polyA template, and 1 U of T7 RNA polymerase incorporates 1 nmol of ATP into RNA in 1 hr at 37° C. using a T7 promoter in a DNA template). All of the reagent addition and mixing steps may be performed manually, using a combination of manual and automated steps, or by using a completely automated system. The amplification methods that use transcription-mediated amplification (TMA) substantially use the procedures already disclosed in detail in U.S. Pat. Nos. 5,399,491 and 5,554,516, Kacian et al., which are incorporated by reference herein. The amplification methods that use single-primer transcription-associated amplification substantially use the procedures already disclosed in detail in US Pub. No. US 2006-0046265, the details of which are incorporated by reference herein. The methods for using hairpin probes are well-known, and include those already disclosed in detail in U.S. Pat. Nos. 6,849,412, 6,835,542, 6,534,274, and 6,361, 945, Becker et al., the details of which are incorporated by reference herein.

By using various combinations of these amplification oligomers and detection probes indicator enterococci 23S rRNA sequences were specifically detected when the sample contained about 100 copies of the 23S rRNA target sequence. The following examples illustrate some of the embodiments of the invention for detection of indicator enterococci 23S rRNA target sequences.

Example 1

Characterization of Detection Probe Oligomers

This example illustrates the characterization of detection probe oligomers by determining their $T_m$ and hybridization characteristics with complementary target sequences. Molecular beacons were synthesized according to standard laboratory procedures using 2'-OMe nucleotide analogs. Hybridization reactions (0.100 mL total volume in 20 mM $MgCl_2$ TRIS-buffered solution) of molecular beacons (10 pmol/reaction) in the absence or presence of synthetic RNA target (30 pmol/reaction of SEQ ID NO: 53 (CAUCAUUCU-CAAUUCCGAGGC)) were incubated 10 min at 60° C., then 60 min at 42° C., measuring fluorescence in relative fluorescence units (RFUs) every 30 sec at 42° C. for 99 cycles using a Rotor-Gene 2000 instrument. After completion, reaction temperatures were increased in one degree Celsius increments from 42-99° C., holding for 15 sec at each step and measuring resulting RFUs to determine $T_m$ of molecular beacons using data analysis software provided by the Rotor-Gene 2000 instrument. Average signal/noise (S/N) ratios were calculated from the measured endpoint RFU in the presence of synthetic RNA target divided by the measured endpoint RFU in the absence of synthetic RNA target.

TABLE 3

Molecular Beacon Melting Temperatures & Hybrid Stability

| Molecular Beacon | $T_m$ without Target (° C.) | $T_m$ with Target (° C.) | S/N Ratio |
|---|---|---|---|
| SEQ ID NO: 11 | 91.3 | 57.3 | 6.6 |
| SEQ ID NO: 13 | 90.1 | 72.4 | 24.1 |
| SEQ ID NO: 15 | 87.4 | 69.1 | 3.8 |
| SEQ ID NO: 17 | 83.6 | 76.1 | 36.1 |
| SEQ ID NO: 19 | 83.2 | 70.6 | 12.7 |
| SEQ ID NO: 21 | 90.3 | 69.6 | 12.7 |

The results demonstrated stable molecular beacon stem structures in the absence of synthetic RNA target, which prevents non-specific opening of the molecular beacons at lower temperatures, and stable hybrid formation of the molecular beacons in the presence of synthetic RNA target under the experimental conditions.

Example 2

Transcription-Mediated Amplification and Detection

This example illustrates amplification and detection assays for indicator enterococci target nucleic acid that detect amplified products in real-time. The amplification reactions were transcription-mediated amplifications that used the procedures described in detail previously (U.S. Pat. Nos. 5,399,491 and 5,554,516, Kacian et al., the details of which are incorporated by reference herein) using some of the amplification oligomer embodiments described above. Each of the assays was performed in an amplification reaction (0.015 mL total volume) that contained the target RNA and amplification reagents substantially as described above, with a promoter-provider oligomer (3 pmol/reaction), a primer oligomer (3 pmol/reaction), and a molecular beacon (3 pmol/reaction). The reaction mixtures containing the amplification oligomers, target and amplification reagents (but not enzymes) were covered to prevent evaporation, incubated 10 min at 60° C., then 2 min at 42° C. Enzymes were then added (in 5 µL vol), the reactions were mixed and incubated at 42° C., measuring fluorescence every 30 sec for 60 cycles during the amplification reaction after enzyme addition.

TABLE 4

Measured Time-of-Emergence
Different Amplification and Detection Probe Oligomer Combinations
$5 \times 10^8$ Copies/Rxn Target

| Amplification Oligomer Combinations | Time-of-Emergence (min) Detection Probe Oligomers | | |
|---|---|---|---|
| | SEQ ID NO: 11 | SEQ ID NO: 13 | SEQ ID NO: 15 |
| SEQ ID NOs: 1 & 9 | 4.6 | 4.5 | 3.3 |
| SEQ ID NOs: 1 & 7 | 5.1 | 4.8 | 3.9 |
| SEQ ID NOs: 1 & 5 | 5.1 | 5.0 | 4.4 |
| SEQ ID NOs: 2 & 9 | 5.0 | 5.6 | 4.2 |
| SEQ ID NOs: 2 & 7 | 5.3 | 5.5 | 4.4 |
| SEQ ID NOs: 2 & 5 | 5.7 | 5.6 | 4.1 |
| SEQ ID NOs: 3 & 9 | 5.6 | 5.4 | 4.2 |
| SEQ ID NOs: 3 & 7 | 4.9 | 5.3 | 3.7 |
| SEQ ID NOs: 3 & 5 | 3.5 | 4.2 | 2.5 |

TABLE 5

Measured Time-of-Emergence
Different Detection Probe Oligomers
Amplification Oligomer SEQ ID NOs: 3 & 5

| Target (copies/rxn) | Time-of-Emergence (min) | | | | | | |
|---|---|---|---|---|---|---|---|
| | SEQ ID NO: 11 | SEQ ID NO: 13 | SEQ ID NO: 15 | SEQ ID NO: 17 | SEQ ID NO: 19 | SEQ ID NO: 21 | SEQ ID NO: 23 |
| $1 \times 10^8$ | 5.2 | 5.5 | 4.2 | 3.0 | 5.1 | 5.3 | 4.3 |
| $1 \times 10^7$ | 6.7 | 7.5 | 5.7 | 4.4 | 6.5 | 7.0 | 6.0 |
| $1 \times 10^6$ | 8.3 | 9.2 | 7.3 | 6.0 | 8.1 | 8.4 | 7.4 |
| $1 \times 10^5$ | 9.4 | 10.6 | 8.7 | 7.2 | 9.4 | 9.8 | 8.7 |
| $1 \times 10^4$ | 11.5 | 12.6 | 10.1 | 8.7 | 11.1 | 11.4 | 10.0 |
| $1 \times 10^3$ | 14.9 | 17.2 | 12.5 | 10.4 | 14.1 | 13.3 | 12.9 |
| $1 \times 10^2$ | 29.9 | 26.1 | 22.2 | 14.6 | 24.3 | 18.4 | 16.8 |

TABLE 6

Measured Time-of-Emergence
Different Amplification Oligomer Combinations
Detection Probe Oligomer SEQ ID NO: 17

| Target (copies/rxn) | Time-of-Emergence (min) | | |
|---|---|---|---|
| | SEQ ID NOs: 1 & 7 | SEQ ID NOs: 1 & 9 | SEQ ID NOs: 3 & 5 |
| $1 \times 10^8$ | 2.5 | 4.3 | 3.0 |
| $1 \times 10^7$ | 3.9 | 5.6 | 4.4 |
| $1 \times 10^6$ | 5.1 | 7.0 | 6.0 |
| $1 \times 10^5$ | 6.5 | 9.3 | 7.2 |
| $1 \times 10^4$ | 9.1 | 15.2 | 8.7 |

TABLE 6-continued

Measured Time-of-Emergence
Different Amplification Oligomer Combinations
Detection Probe Oligomer SEQ ID NO: 17

| Target (copies/rxn) | Time-of-Emergence (min) | | |
|---|---|---|---|
| | SEQ ID NOs: 1 & 7 | SEQ ID NOs: 1 & 9 | SEQ ID NOs: 3 & 5 |
| $1 \times 10^3$ | 16.4 | ND | 10.4 |
| $1 \times 10^2$ | ND | ND | 14.6 |

ND = Not Detected

The results of these experiments demonstrated a sensitivity at 100 copies using various amplification and detection probe oligomer combinations.

Example 3

Single-Primer Transcription-Mediated Amplification and Detection

This example illustrates amplification and detection assays for indicator enterococci target nucleic acid that detect amplified products in real-time. The amplification reactions were single-primer transcription-mediated amplifications that used the procedures described in detail previously (US Pub. No. 2006-0046265, the details of which are incorporated by reference herein) using some of the amplification oligomer embodiments described above. Each of the assays was performed in an amplification reaction (0.040 mL total volume) that contained the target RNA and amplification reagents substantially as described above, with a promoter-provider oligomer (12 pmol/reaction), a primer oligomer (12 pmol/reaction), a blocker oligomer (0.8 pmol/reaction), and a molecular torch (6 pmol/reaction). Promoter-provider SEQ ID NOs: 32 and 34 correspond with blocker oligomer SEQ ID NO: 54 (CCGCUACCCACACCUCAUCC). Promoter-provider SEQ ID NO: 38 corresponds with blocker oligomer SEQ ID NO: 55 (CUAUCUCCAAGUUCGUUUGGAAU-UUC) and promoter-provider SEQ ID NO: 40 corresponds with blocker oligomer SEQ ID NO: 56 (CAAGUUCGU-UUGGAAUUUCUCCG). The reaction mixtures containing the amplification oligomers, target and amplification reagents (but not enzymes) were covered to prevent evaporation, incubated 10 min at 60° C., then 5 min at 42° C. Enzymes were then added (in 10 μL vol), the reactions were mixed and incubated for 5 min at 42° C., measuring fluorescence every 30 sec during the amplification reaction after enzyme addition.

TABLE 7

Measured Time-of-Emergence
Different Amplification Oligomer Combinations
Detection Probe Oligomer SEQ ID NO: 44

| Target (copies/rxn) | Time-of-Emergence (min) | | | |
|---|---|---|---|---|
| | SEQ ID NOs: 26 & 38 | SEQ ID NOs: 26 & 40 | SEQ ID NOs: 28 & 38 | SEQ ID NOs: 28 & 40 |
| 0 | ND | ND | ND | ND |
| 100 | ND | ND | ND | ND |
| 1000 | ND | ND | ND | ND |

TABLE 7-continued

Measured Time-of-Emergence
Different Amplification Oligomer Combinations
Detection Probe Oligomer SEQ ID NO: 44

| Target (copies/rxn) | Time-of-Emergence (min) | | | |
|---|---|---|---|---|
| | SEQ ID NOs: 26 & 38 | SEQ ID NOs: 26 & 40 | SEQ ID NOs: 28 & 38 | SEQ ID NOs: 28 & 40 |
| 10,000 | 28.3 | 27.9 | ND | ND |
| 100,000 | 25.9 | 26.4 | 34.5 | ND |

ND = Not Detected

The results of this assay demonstrated a sensitivity at 10,000 copies with SEQ ID NO: 26 having much better performance than SEQ ID NO: 28 as a primer oligomer.

TABLE 8

Measured Time-of-Emergence
Different Amplification and Detection Probe Oligomer Combinations
Amplification Oligomer SEQ ID NO: 26

| Target (copies/rxn) | Time-of-Emergence (min) | | | |
|---|---|---|---|---|
| | SEQ ID NOs: 32 & 44 | SEQ ID NOs: 32 & 48 | SEQ ID NOs: 34 & 44 | SEQ ID NOs: 34 & 48 |
| 0 | ND | ND | ND | ND |
| 1000 | 19.2 | ND | 21.5 | ND |
| 10,000 | 17.3 | ND | 20.5 | ND |
| 100,000 | 15.6 | ND | 18.0 | ND |

ND = Not Detected

The results of this assay demonstrated a sensitivity at 1000 copies with SEQ ID NO: 44 having much better performance than SEQ ID NO: 48 as a molecular torch. SEQ ID NO: 48 failed to open.

TABLE 9

Measured Time-of-Emergence
Different Amplification Oligomer Combinations
Detection Probe Oligomer SEQ ID NO: 44

| Target (copies/rxn) | Time-of-Emergence (min) | | |
|---|---|---|---|
| | SEQ ID NOs: 27 & 32 | SEQ ID NOs: 27 & 36 | SEQ ID NOs: 27 & 40 |
| 0 | ND | ND | ND |
| 1000 | 23.6 | 27.4 | 34.6 |
| 10,000 | 19.6 | 20.7 | 29.9 |
| 100,000 | 18.3 | 19.9 | 28.4 |

ND = Not Detected

The results of this assay demonstrated a sensitivity of 1000 copies with SEQ ID NO: 32 having much better performance than either SEQ ID NO: 36 or SEQ ID NO: 40 as a promoter-provider oligomer.

TABLE 10

Measured Time-of-Emergence
Different Amplification and Detection Probe Oligomer Combinations
Amplification Oligomer SEQ ID NO: 26

| Target (copies/rxn) | Time-of-Emergence (min) | | |
|---|---|---|---|
| | SEQ ID NOs: 32 & 42 | SEQ ID NOs: 32 & 44 | SEQ ID NOs: 32 & 46 |
| 0 | ND | ND | 38.5* |
| 1000 | 30.1 | 25.0 | 22.8 |
| 10,000 | 26.2 | 22.8 | 19.6 |
| 100,000 | 25.0 | 21.3 | 17.5 |

ND = Not Detected
*= Result of low level contamination

The results of this assay demonstrated a sensitivity at 1000 copies with SEQ ID NO: 46 having much better performance than either SEQ ID NO: 42 or SEQ ID NO: 44 as a molecular torch.

TABLE 11

Measured Time-of-Emergence
Different Amplification Oligomer Combinations
Detection Probe Oligomer SEQ ID NO: 46

| Target (copies/rxn) | Time-of-Emergence (min) | | |
|---|---|---|---|
| | SEQ ID NOs: 26 & 32 | SEQ ID NOs: 29 & 32 | SEQ ID NOs: 30 & 32 |
| 0 | 46.4 | 40.9 | 45.1 |
| 1000 | 22.9 | 25.3 | 23.8 |
| 10,000 | 20.4 | 22.0 | 21.2 |

The results of this assay demonstrated a sensitivity at 1000 copies with SEQ ID NOs: 26 and 30 having much better performance than SEQ ID NO: 29 as a primer oligomer.

Collectively, the results of the assays demonstrated a preferred combination of SEQ ID NOs: 30, 32 and 46 for real-time detection of indicator enterococci 23S rRNA target.

Example 4

Specificity and Cross-Reactivity

This example demonstrates the specificity of the amplification and detection assays described herein for indicator enterococci target nucleic acid. The amplification reactions were real-time single-primer transcription-mediated amplifications that used the procedures described in detail previously (US Pub. No. 2006-0046265, the details of which are incorporated by reference herein) using the following combination of oligomers: SEQ ID NO: 30 (6 pmol/reaction); SEQ ID NO: 32 (12 pmol/reaction); SEQ ID NO: 46 (6 pmol/reaction); and, SEQ ID NO: 54 (0.5 pmol/reaction). Sample solutions of at least $10^8$ CFU of selected enterococcal and non-enterococcal organisms were prepared in 100 mL sterile saline. The samples were filtered through a membrane (0.45 μm) and washed with polyvinylpyrrolidone (50 mL at 3% w/v). Retained bacteria were lysed using lysis reagents substantially as described above (1 mL each) with incubation for 10 min at 37° C. between reagent additions. Released indicator enterococci 23S rRNA was isolated from the resulting lysate (1 mL) by addition of target capture reagent substantially as described above (50 μL), incubation for 5 min at 60° C., cooling for 10 min at room temperature, sequential washings with wash solution substantially as described above (1 mL, 0.5 mL, 0.1 mL), followed by elution from the magnetic particles with nuclease-free water (60 μL). Indicator enterococci 23S rRNA (10 μL) was then assayed in amplification reactions (0.04 mL total volume) using amplification reagents substantially as described above, but with the following modifications: omission of glycerol, EDTA and N-acetyl-L-cysteine; and, increased concentration of magnesium chloride from 23 to 30 mM. The reaction mixtures containing the amplification oligomers, target and amplification reagents (but not enzymes) were covered to prevent evaporation, incubated 10 min at 60° C., then 5 min at 42° C. Enzymes were then added (10 μL), the reactions were mixed and incubated at 42° C., measuring fluorescence every 30 sec for 35 min during the amplification reaction after enzyme addition.

TABLE 12

Measured Time-of-Emergence
*Enterococcus* Species

| | Culture Count (CFU/mL) | Mean Time-of-Emergence (min) | Mean Time-of-Emergence (min) |
|---|---|---|---|
| E. faecalis | $4.85 \times 10^8$ | 10.7 | 10.1 |
| E. faecalis Variant 1 | $10.60 \times 10^8$ | 9.8 | 8.0 |
| E. faecalis Variant 2 | $9.65 \times 10^8$ | 8.9 | 7.9 |
| E. faecium | $3.70 \times 10^8$ | 9.7 | 9.9 |
| E. casseliflavus | $7.25 \times 10^8$ | 10.7 | 10.0 |
| E. gallinarum | $6.70 \times 10^8$ | 9.8 | 10.2 |
| E. mundtii | $4.90 \times 10^8$ | 9.1 | 9.4 |
| E. dispar | $3.00 \times 10^8$ | ND | ND |
| E. durans | $5.25 \times 10^8$ | 10.4 | 10.4 |
| E. hirae | $5.45 \times 10^8$ | 10.1 | 10.1 |
| E. columbae | $3.00 \times 10^8$ | 14.0 | 13.0 |
| E. avium | $2.55 \times 10^8$ | ND | ND |
| E. malodoratus | $2.30 \times 10^8$ | ND | ND |
| E. pseudoavium | $5.45 \times 10^8$ | ND | ND |
| E. raffinosus | $5.45 \times 10^8$ | ND | ND |
| E. saccharolyticus | $3.00 \times 10^8$ | ND | ND |

TABLE 13

Measured Time-of-Emergence
Non-*Enterococcus* Species

| Organism | Culture Count (CFU/mL) | Mean Time-of-Emergence (min) | Mean Time-of-Emergence (min) |
|---|---|---|---|
| Carnobacterium pisciola | $2.25 \times 10^8$ | ND | ND |
| Lactobacillus casei | $1.15 \times 10^8$ | ND | ND |
| Lactobacillus ruminis | $1.75 \times 10^8$ | 15.2 | 15.5 |
| Lactococcus lactis | $11.40 \times 10^8$ | 33.6 | 33.0 |
| Listeria monocytogenes | $0.40 \times 10^8$ | ND | ND |
| Streptococcus salivarius | $8.80 \times 10^8$ | 66.2 | 64.4 |
| Streptococcus uberis | $3.00 \times 10^8$ | 27.5 | 26.8 |

Similarly, $10^6$ CFU *Streptococcus bovis* was compared to $10^6$ and 10 CFU *E. faecalis*. *S bovis* was not detected whereas *E. faecalis* yielded mean emergence times of 23.12 and 57.30 min, respectively. Similar sized colonies of *E. faecalis*, *Aerococcus viridans*, *Ralstonia pickettii*, and *Staphylococcus epidermidis* grown on nutrient agar were also compared. *E. faecalis* yielded an emergence time of 19.15 min whereas the other organisms were not detected.

Collectively, the results demonstrate specificity for *E. faecalis*, *E. faecium*, *E. casseliflavus*, *E. gallinarum*, *E. mundtii*, *E. durans*, *E. hirae*, and *E. columbae* without detection of *E. avium*, *E. malodoratus*, *E. pseudoavium*, *E. raffinosus*, *E. saccharolyticus*, and *E. dispar*. Although some cross-reactivity was observed with *Lactobacillus ruminis, Lactococcus lactis, Streptococcus salivarius* and *Streptococcus uberis*, such organisms should not interfere with the amplification and detection of indicator enterococci in recreational water samples unless present in abnormally high concentrations.

Example 5

Single-Primer Transcription-Mediated Amplification and Detection of Target and Internal Control This example illustrates amplification and detection assays for indicator enterococci target nucleic acid and non-enterococci internal control (IC) nucleic acid. The example also demonstrates the effectiveness of the non-enterococci IC nucleic acid in detecting non-specific amplification failure. The amplification reactions were real-time single-primer transcription-mediated amplifications that used the procedures described in detail previously (US Pub. No. 2006-0046265, the details of which are incorporated by reference herein) using the following combination of oligomers for indicator enterococci target nucleic acid: SEQ ID NO: 30 (6 pmol/reaction); SEQ ID NO: 32 (12 pmol/reaction); SEQ ID NO: 46 (6 pmol/reaction); and, SEQ ID NO: 54 (0.5 pmol/reaction). Indicator enterococci target nucleic acid and non-enterococci IC nucleic acid (500 pg each in 10 µL final volume) were assayed in amplification reactions (0.04 mL total volume) using amplification reagents substantially as described in Example 4 but with the addition in various proportions of excess wash solution, which is known to inhibit amplification. The reaction mixtures containing the amplification oligomers, target, IC and amplification reagents (but not enzymes) were covered to prevent evaporation, incubated 10 min at 60° C. and then cooled to 2° C. Enzymes were then added (10 µL), the reactions were mixed and incubated at 42° C., measuring fluorescence every 30 sec for 35 min during the amplification reaction after enzyme addition.

TABLE 14

Measured Time-of-Emergence
Inhibitor Effect on Target and Internal Control

| % (v/v) Wash Solution | Target | Internal Control |
|---|---|---|
| 0 | 17.94 | 21.90 |
| 6 | 20.97 | 25.48 |
| 19 | 26.47 | 31.40 |
| 25 | 32.23 | 36.90 |

Example 6

Automated Target Capture

This example demonstrates use of a commercially available automated platform, the KingFisher 96 from Thermo Scientific, for capturing indicator enterococci target nucleic acid and non-enterococci internal control (IC) nucleic acid for subsequent amplification and detection. Sample solutions containing known numbers of indicator enterococci were prepared in 100 mL sterile saline. The samples were filtered through a membrane (0.45 µm) and washed with polyvinylpyrrolidone (50 mL at 3% w/v). Retained bacteria were lysed using lysis reagents substantially as described above (1 mL each) with incubation for 10 min at 37° C. between reagent additions. Treated samples of released indicator enterococci 23S rRNA (1 mL) were then transferred to a deep 96-well microtiter plate where target capture reagent substantially as described above (50 µL) with 62.5 pg of non-enterococci IC nucleic acid was added. Resulting mixtures were loaded onto a Kingfisher 96 that was programmed to heat the plate for 5 min at 60° C., cool for 10 min at room temperature, capture the particles, and perform two sequential washings with wash solution substantially as described above, followed by elution of the nucleic acids from the magnetic particles with nuclease-free water (60 µL). A portion of each eluate (10 µL) was then used in amplification and detection assays substantially as described above.

TABLE 15

Measured Time-of-Emergence
Automated Target Capture

| Enterococci (CFU/100 mL) | Target | Internal Control |
|---|---|---|
| 0 | 62.16 | 27.15 |
| 10 | 31.65 | 26.31 |
| 100 | 27.06 | 27.96 |
| 1000 | 23.81 | 25.63 |

The invention claimed is:

1. A method for amplifying and detecting indicator enterococci nucleic acid in a sample, wherein said indicator enterococci nucleic acid is nucleic acid from *E. faecalis, E. faecium, E. casseliflavus, E. gallinarum, E. mundtii, E. durans, E. hirae* and/or *E. columbae* and not from *E. avium, E. malodoratus, E. pseudoavium, E. raffinosus, E. saccharolyticus* or *E. dispar*, comprising the steps of:
   a) contacting said sample with a first amplification oligomer comprising a target binding region consisting of SEQ ID NO: 30, a second amplification oligomer comprising a target binding region consisting of SEQ ID NO: 31, and a detection probe oligomer comprising a target binding region consisting of SEQ ID NO: 45;
   b) exposing said sample to conditions sufficient to amplify indicator *enterococci* nucleic acid if present in said sample with said first and second amplification oligomers to produce an amplified product; and
   c) determining whether said indicator enterococci nucleic acid is in said sample by using said detection probe oligomer to detect the presence or absence of the amplified product.

2. The method of claim 1, wherein said detection probe oligomer comprises at least one non-target binding region.

3. The method of claim 2, wherein said detection probe oligomer comprises two non-target binding regions tat hybridize to each other when said detection probe oligomer is not hybridized to indicator *enterococci* nucleic acid.

4. The method of claim 1, 2 or 3, wherein said detection probe oligomer comprises a detectable label.

5. The method of claim 4, wherein said detection probe oligomer comprises a fluprophore and a quencher.

6. The method of claim 1, wherein said second amplification oligomer comprises a promoter sequence.

7. The method of claim 6, wherein said promoter sequence consists of SEQ ID NO: 49.

8. A kit for amplifying and detecting indicator enterococci nucleic acid in a sample, wherein said indicator enterococci nucleic acid is nucleic acid from *E. faecalis, E. faecium, E. casseliflavus, E. gallinarum, E. mundtii, E. durans, E. hirae* and/or *E. columbae* and not from *E. avium, E. malodoratus, E. pseudoavium, E. raffinosus, E. saccharolyticus* or *E. disbar*, comprising:
   a first amplification oligomer 27-100 nucleotides in length comprising a target binding region consisting of SEQ ID NO: 30; a second amplification oligomer 34-100 nucleotides in length comprising a target binding region consisting of SEQ ID NO: 31; and a detection probe oligomer 15-100 nucleotides in length comprising a target binding region consisting of SEQ ID NO: 45.

9. The kit of claim 8, wherein said detection probe oligomer 15-100 nucleotides in length comprises at least one non-target binding region.

10. The kit of claim 9, wherein said detection probe oligomer 15-100 nucleotides in length comprises two non-target binding regions that hybridize to each other when said detection probe oligomer is not hybridized to indicator enterococci nucleic acid.

11. The kit of claim 8, 9 or 10, wherein said detection probe oligomer 15-100 nucleotides in length comprises a detectable label.

12. The kit of claim 11, wherein said detection probe oligomer 15-100 nucleotides in length comprises a fluorophore and a quencher.

13. The kit of claim 8, wherein said second amplification oligomer 34-100 nucleotides in length comprises a promoter sequence.

14. The kit of claim 13, wherein said promoter sequence consists of SEQ ID NO: 49.

15. The kit of claim 8, further comprising a capture oligomer.

16. The kit of claim 15, wherein said capture oligomer comprises SEQ ID NO: 50, 51 or 52.

17. The method of claim 1, wherein the sample is an enviromnental sample or a biological sample.

18. The method of claim 1, wherein the sample is a processed sample.

* * * * *

SEQUENCE LISTING

<160> NUMBER OF SEQ ID NOS: 56

<210> SEQ ID NO 1
<211> LENGTH: 19
<212> TYPE: DNA
<213> ORGANISM: Artificial
<220> FEATURE:
<223> OTHER INFORMATION: synthetic oligonucleotide

<400> SEQUENCE: 1
gagatagctg gttctctcc                                              19

-continued

<210> SEQ ID NO 2
<211> LENGTH: 20
<212> TYPE: DNA
<213> ORGANISM: Artificial
<220> FEATURE:
<223> OTHER INFORMATION: synthetic oligonucleotide

<400> SEQUENCE: 2
gagatagctg gttctctccg                                              20

<210> SEQ ID NO 3
<211> LENGTH: 21
<212> TYPE: DNA
<213> ORGANISM: Artificial
<220> FEATURE:
<223> OTHER INFORMATION: synthetic oligonucleotide

<400> SEQUENCE: 3
gagatagctg gttctctccg a                                            21

<210> SEQ ID NO 4
<211> LENGTH: 22
<212> TYPE: DNA
<213> ORGANISM: Artificial
<220> FEATURE:
<223> OTHER INFORMATION: synthetic oligonucleotide

<400> SEQUENCE: 4
cctagtccaa acagtgctct ac                                           22

<210> SEQ ID NO 5
<211> LENGTH: 49
<212> TYPE: DNA
<213> ORGANISM: Artificial
<220> FEATURE:
<223> OTHER INFORMATION: synthetic oligonucleotide

<400> SEQUENCE: 5
aatttaatac gactcactat agggagacct agtccaaaca gtgctctac              49

<210> SEQ ID NO 6
<211> LENGTH: 24
<212> TYPE: DNA
<213> ORGANISM: Artificial
<220> FEATURE:
<223> OTHER INFORMATION: synthetic oligonucleotide

<400> SEQUENCE: 6
ccctagtcca acagtgctc tacc                                          24

<210> SEQ ID NO 7
<211> LENGTH: 51
<212> TYPE: DNA
<213> ORGANISM: Artificial
<220> FEATURE:
<223> OTHER INFORMATION: synthetic oligonucleotide

<400> SEQUENCE: 7
aatttaatac gactcactat agggagaccc tagtccaaac agtgctctac c            51

<210> SEQ ID NO 8
<211> LENGTH: 26
<212> TYPE: DNA
<213> ORGANISM: Artificial
<220> FEATURE:
<223> OTHER INFORMATION: synthetic oligonucleotide

```
<400> SEQUENCE: 8
ccctagtcca aacagtgctc tacctc                                          26

<210> SEQ ID NO 9
<211> LENGTH: 53
<212> TYPE: DNA
<213> ORGANISM: Artificial
<220> FEATURE:
<223> OTHER INFORMATION: synthetic oligonucleotide

<400> SEQUENCE: 9
aatttaatac gactcactat agggagaccc tagtccaaac agtgctctac ctc            53

<210> SEQ ID NO 10
<211> LENGTH: 16
<212> TYPE: RNA
<213> ORGANISM: Artificial
<220> FEATURE:
<223> OTHER INFORMATION: synthetic oligonucleotide

<400> SEQUENCE: 10
cucggaauug agaaug                                                     16

<210> SEQ ID NO 11
<211> LENGTH: 26
<212> TYPE: RNA
<213> ORGANISM: Artificial
<220> FEATURE:
<223> OTHER INFORMATION: synthetic oligonucleotide

<400> SEQUENCE: 11
ccgagcucgg aauugagaau gcucgg                                          26

<210> SEQ ID NO 12
<211> LENGTH: 17
<212> TYPE: RNA
<213> ORGANISM: Artificial
<220> FEATURE:
<223> OTHER INFORMATION: synthetic oligonucleotide

<400> SEQUENCE: 12
ccucggaauu gagaaug                                                    17

<210> SEQ ID NO 13
<211> LENGTH: 27
<212> TYPE: RNA
<213> ORGANISM: Artificial
<220> FEATURE:
<223> OTHER INFORMATION: synthetic oligonucleotide

<400> SEQUENCE: 13
ccgagccucg gaauugagaa ugcucgg                                         27

<210> SEQ ID NO 14
<211> LENGTH: 17
<212> TYPE: RNA
<213> ORGANISM: Artificial
<220> FEATURE:
<223> OTHER INFORMATION: synthetic oligonucleotide

<400> SEQUENCE: 14
cucggaauug agaauga                                                    17

<210> SEQ ID NO 15
```

```
<211> LENGTH: 27
<212> TYPE: RNA
<213> ORGANISM: Artificial
<220> FEATURE:
<223> OTHER INFORMATION: synthetic oligonucleotide

<400> SEQUENCE: 15
ccgagcucgg aauugagaau gacucgg                                              27

<210> SEQ ID NO 16
<211> LENGTH: 18
<212> TYPE: RNA
<213> ORGANISM: Artificial
<220> FEATURE:
<223> OTHER INFORMATION: synthetic oligonucleotide

<400> SEQUENCE: 16
ccucggaauu gagaauga                                                        18

<210> SEQ ID NO 17
<211> LENGTH: 28
<212> TYPE: RNA
<213> ORGANISM: Artificial
<220> FEATURE:
<223> OTHER INFORMATION: synthetic oligonucleotide

<400> SEQUENCE: 17
ccgagccucg gaauugagaa ugacucgg                                             28

<210> SEQ ID NO 18
<211> LENGTH: 18
<212> TYPE: RNA
<213> ORGANISM: Artificial
<220> FEATURE:
<223> OTHER INFORMATION: synthetic oligonucleotide

<400> SEQUENCE: 18
cucggaauug agaaugau                                                        18

<210> SEQ ID NO 19
<211> LENGTH: 28
<212> TYPE: RNA
<213> ORGANISM: Artificial
<220> FEATURE:
<223> OTHER INFORMATION: synthetic oligonucleotide

<400> SEQUENCE: 19
ccgagcucgg aauugagaau gaucucgg                                             28

<210> SEQ ID NO 20
<211> LENGTH: 19
<212> TYPE: RNA
<213> ORGANISM: Artificial
<220> FEATURE:
<223> OTHER INFORMATION: synthetic oligonucleotide

<400> SEQUENCE: 20
cucggaauug agaaugaug                                                       19

<210> SEQ ID NO 21
<211> LENGTH: 29
<212> TYPE: RNA
<213> ORGANISM: Artificial
<220> FEATURE:
<223> OTHER INFORMATION: synthetic oligonucleotide

<400> SEQUENCE: 21
```

```
ccgagcucgg aauugagaau gaugcucgg                              29
```

<210> SEQ ID NO 22
<211> LENGTH: 19
<212> TYPE: RNA
<213> ORGANISM: Artificial
<220> FEATURE:
<223> OTHER INFORMATION: synthetic oligonucleotide

<400> SEQUENCE: 22

```
ccucggaauu gagaaugau                                         19
```

<210> SEQ ID NO 23
<211> LENGTH: 29
<212> TYPE: RNA
<213> ORGANISM: Artificial
<220> FEATURE:
<223> OTHER INFORMATION: synthetic oligonucleotide

<400> SEQUENCE: 23

```
ccgagccucg gaauugagaa ugaucucgg                              29
```

<210> SEQ ID NO 24
<211> LENGTH: 19
<212> TYPE: RNA
<213> ORGANISM: Artificial
<220> FEATURE:
<223> OTHER INFORMATION: synthetic oligonucleotide

<400> SEQUENCE: 24

```
gccucggaau ugagaauga                                         19
```

<210> SEQ ID NO 25
<211> LENGTH: 29
<212> TYPE: RNA
<213> ORGANISM: Artificial
<220> FEATURE:
<223> OTHER INFORMATION: synthetic oligonucleotide

<400> SEQUENCE: 25

```
ccgaggccuc ggaauugaga augacucgg                              29
```

<210> SEQ ID NO 26
<211> LENGTH: 22
<212> TYPE: DNA
<213> ORGANISM: Artificial
<220> FEATURE:
<223> OTHER INFORMATION: synthetic oligonucleotide

<400> SEQUENCE: 26

```
cctagtccaa acagtgctct ac                                     22
```

<210> SEQ ID NO 27
<211> LENGTH: 22
<212> TYPE: DNA
<213> ORGANISM: Artificial
<220> FEATURE:
<223> OTHER INFORMATION: synthetic oligonucleotide

<400> SEQUENCE: 27

```
gatgggcccc tagtccaaac ag                                     22
```

<210> SEQ ID NO 28
<211> LENGTH: 22
<212> TYPE: DNA

```
<213> ORGANISM: Artificial
<220> FEATURE:
<223> OTHER INFORMATION: synthetic oligonucleotide

<400> SEQUENCE: 28
ctgaattcgg taacccgaga tg                                              22

<210> SEQ ID NO 29
<211> LENGTH: 29
<212> TYPE: DNA
<213> ORGANISM: Artificial
<220> FEATURE:
<223> OTHER INFORMATION: synthetic oligonucleotide

<400> SEQUENCE: 29
gguaacccga gatgggcccc tagtccaaa                                       29

<210> SEQ ID NO 30
<211> LENGTH: 27
<212> TYPE: DNA
<213> ORGANISM: Artificial
<220> FEATURE:
<223> OTHER INFORMATION: synthetic oligonucleotide

<400> SEQUENCE: 30
cgagatgggc ccctagtcca aacagtg                                         27

<210> SEQ ID NO 31
<211> LENGTH: 34
<212> TYPE: DNA
<213> ORGANISM: Artificial
<220> FEATURE:
<223> OTHER INFORMATION: synthetic oligonucleotide

<400> SEQUENCE: 31
gtagcggaga aattccaaac gaacttggag atag                                 34

<210> SEQ ID NO 32
<211> LENGTH: 61
<212> TYPE: DNA
<213> ORGANISM: Artificial
<220> FEATURE:
<223> OTHER INFORMATION: synthetic oligonucleotide

<400> SEQUENCE: 32
aatttaatac gactcactat agggagagta gcggagaaat tccaaacgaa cttggagata    60
g                                                                     61

<210> SEQ ID NO 33
<211> LENGTH: 40
<212> TYPE: DNA
<213> ORGANISM: Artificial
<220> FEATURE:
<223> OTHER INFORMATION: synthetic oligonucleotide

<400> SEQUENCE: 33
gtagcggaga aattccaaac gaacttggag atagccacaa                           40

<210> SEQ ID NO 34
<211> LENGTH: 67
<212> TYPE: DNA
<213> ORGANISM: Artificial
<220> FEATURE:
<223> OTHER INFORMATION: synthetic oligonucleotide

<400> SEQUENCE: 34
```

```
aatttaatac gactcactat agggagagta gcggagaaat tccaaacgaa cttggagata    60
gccacaa                                                              67

<210> SEQ ID NO 35
<211> LENGTH: 46
<212> TYPE: DNA
<213> ORGANISM: Artificial
<220> FEATURE:
<223> OTHER INFORMATION: synthetic oligonucleotide

<400> SEQUENCE: 35
gtagcggaga aattccaaac gaacttggag atagctggtt ctctcc                   46

<210> SEQ ID NO 36
<211> LENGTH: 73
<212> TYPE: DNA
<213> ORGANISM: Artificial
<220> FEATURE:
<223> OTHER INFORMATION: synthetic oligonucleotide

<400> SEQUENCE: 36
aatttaatac gactcactat agggagagta gcggagaaat tccaaacgaa cttggagata    60
gctggttctc tcc                                                       73

<210> SEQ ID NO 37
<211> LENGTH: 33
<212> TYPE: DNA
<213> ORGANISM: Artificial
<220> FEATURE:
<223> OTHER INFORMATION: synthetic oligonucleotide

<400> SEQUENCE: 37
gagatagctg gttctctccg aaatagcttt agg                                 33

<210> SEQ ID NO 38
<211> LENGTH: 60
<212> TYPE: DNA
<213> ORGANISM: Artificial
<220> FEATURE:
<223> OTHER INFORMATION: synthetic oligonucleotide

<400> SEQUENCE: 38
aatttaatac gactcactat agggagagag atagctggtt ctctccgaaa tagctttagg    60

<210> SEQ ID NO 39
<211> LENGTH: 31
<212> TYPE: DNA
<213> ORGANISM: Artificial
<220> FEATURE:
<223> OTHER INFORMATION: synthetic oligonucleotide

<400> SEQUENCE: 39
acttggagat agctggttct ctccgaaata g                                   31

<210> SEQ ID NO 40
<211> LENGTH: 58
<212> TYPE: DNA
<213> ORGANISM: Artificial
<220> FEATURE:
<223> OTHER INFORMATION: synthetic oligonucleotide

<400> SEQUENCE: 40
aatttaatac gactcactat agggagaact tggagatagc tggttctctc cgaaatag      58
```

```
<210> SEQ ID NO 41
<211> LENGTH: 16
<212> TYPE: RNA
<213> ORGANISM: Artificial
<220> FEATURE:
<223> OTHER INFORMATION: synthetic oligonucleotide

<400> SEQUENCE: 41
ccuccaucau ucucaa                                                        16

<210> SEQ ID NO 42
<211> LENGTH: 23
<212> TYPE: RNA
<213> ORGANISM: Artificial
<220> FEATURE:
<223> OTHER INFORMATION: synthetic oligonucleotide

<400> SEQUENCE: 42
cccuccauca uucucaagga ggg                                                23

<210> SEQ ID NO 43
<211> LENGTH: 15
<212> TYPE: RNA
<213> ORGANISM: Artificial
<220> FEATURE:
<223> OTHER INFORMATION: synthetic oligonucleotide

<400> SEQUENCE: 43
ccaucauucu caauu                                                         15

<210> SEQ ID NO 44
<211> LENGTH: 22
<212> TYPE: RNA
<213> ORGANISM: Artificial
<220> FEATURE:
<223> OTHER INFORMATION: synthetic oligonucleotide

<400> SEQUENCE: 44
cccaucauuc ucaauugaug gg                                                 22

<210> SEQ ID NO 45
<211> LENGTH: 15
<212> TYPE: RNA
<213> ORGANISM: Artificial
<220> FEATURE:
<223> OTHER INFORMATION: synthetic oligonucleotide

<400> SEQUENCE: 45
cucaauuccg aggcu                                                         15

<210> SEQ ID NO 46
<211> LENGTH: 22
<212> TYPE: RNA
<213> ORGANISM: Artificial
<220> FEATURE:
<223> OTHER INFORMATION: synthetic oligonucleotide

<400> SEQUENCE: 46
cccucaauuc cgaggcugag gg                                                 22

<210> SEQ ID NO 47
<211> LENGTH: 14
<212> TYPE: RNA
<213> ORGANISM: Artificial
<220> FEATURE:
<223> OTHER INFORMATION: synthetic oligonucleotide
```

```
<400> SEQUENCE: 47
uccgaggcua gccc                                                    14

<210> SEQ ID NO 48
<211> LENGTH: 19
<212> TYPE: RNA
<213> ORGANISM: Artificial
<220> FEATURE:
<223> OTHER INFORMATION: synthetic oligonucleotide

<400> SEQUENCE: 48
cuccgaggcu agcccggag                                               19

<210> SEQ ID NO 49
<211> LENGTH: 27
<212> TYPE: DNA
<213> ORGANISM: Artificial
<220> FEATURE:
<223> OTHER INFORMATION: synthetic oligonucleotide

<400> SEQUENCE: 49
aatttaatac gactcactat agggaga                                      27

<210> SEQ ID NO 50
<211> LENGTH: 26
<212> TYPE: RNA
<213> ORGANISM: Artificial
<220> FEATURE:
<223> OTHER INFORMATION: synthetic oligonucleotide

<400> SEQUENCE: 50
ccaccgugcg cccuuauuca cuuaac                                       26

<210> SEQ ID NO 51
<211> LENGTH: 25
<212> TYPE: RNA
<213> ORGANISM: Artificial
<220> FEATURE:
<223> OTHER INFORMATION: synthetic oligonucleotide

<400> SEQUENCE: 51
gauguuucag uucucugcgu cuacc                                        25

<210> SEQ ID NO 52
<211> LENGTH: 24
<212> TYPE: RNA
<213> ORGANISM: Artificial
<220> FEATURE:
<223> OTHER INFORMATION: synthetic oligonucleotide

<400> SEQUENCE: 52
cgcucgccgc uacucaggga aucg                                         24

<210> SEQ ID NO 53
<211> LENGTH: 21
<212> TYPE: RNA
<213> ORGANISM: Artificial
<220> FEATURE:
<223> OTHER INFORMATION: synthetic oligonucleotide

<400> SEQUENCE: 53
caucauucuc aauuccgagg c                                            21

<210> SEQ ID NO 54
```

```
<211> LENGTH: 20
<212> TYPE: RNA
<213> ORGANISM: Artificial
<220> FEATURE:
<223> OTHER INFORMATION: synthetic oligonucleotide

<400> SEQUENCE: 54
ccgcuaccca caccucaucc                                                    20

<210> SEQ ID NO 55
<211> LENGTH: 26
<212> TYPE: RNA
<213> ORGANISM: Artificial
<220> FEATURE:
<223> OTHER INFORMATION: synthetic oligonucleotide

<400> SEQUENCE: 55
cuaucuccaa guucguuugg aauuuc                                             26

<210> SEQ ID NO 56
<211> LENGTH: 23
<212> TYPE: RNA
<213> ORGANISM: Artificial
<220> FEATURE:
<223> OTHER INFORMATION: synthetic oligonucleotide

<400> SEQUENCE: 56
caaguucguu uggaauuucu ccg                                                23
```